United States Patent
Toyoshima et al.

(10) Patent No.: US 9,229,018 B2
(45) Date of Patent: Jan. 5, 2016

(54) SAMPLE ANALYZER AND SAMPLE ANALYZING METHOD

(75) Inventors: Hiroto Toyoshima, Kobe (JP); Kazunori Mototsu, Kobe (JP)

(73) Assignee: SYSMEX CORPORATION, Kobe-Shi (JP)

( * ) Notice: Subject to any disclaimer, the term of this patent is extended or adjusted under 35 U.S.C. 154(b) by 1003 days.

(21) Appl. No.: 13/315,884

(22) Filed: Dec. 9, 2011

(65) Prior Publication Data

US 2012/0149127 A1    Jun. 14, 2012

(30) Foreign Application Priority Data

Dec. 14, 2010 (JP) ............................. JP2010-278440

(51) Int. Cl.
*G01N 1/18* (2006.01)
*G01N 35/00* (2006.01)
*G01N 35/10* (2006.01)

(52) U.S. Cl.
CPC ........ *G01N 35/0098* (2013.01); *G01N 35/1002* (2013.01); *Y10T 436/25375* (2015.01)

(58) Field of Classification Search
CPC .......... G01N 35/0098; G01N 35/1002; G01N 35/0099; G01N 1/405; Y10T 436/25375
See application file for complete search history.

(56) References Cited

U.S. PATENT DOCUMENTS

| 7,033,820 B2 | 4/2006 | Ammann et al. |
| 2006/0204997 A1* | 9/2006 | Macioszek et al. ............... 435/6 |
| 2007/0172390 A1 | 7/2007 | Ootani et al. |
| 2008/0206099 A1 | 8/2008 | Aruga et al. |
| 2008/0311678 A1 | 12/2008 | Ootani et al. |

FOREIGN PATENT DOCUMENTS

| JP | 2001-091521 A | 4/2001 |
| JP | 2007-300930 | 11/2007 |

* cited by examiner

*Primary Examiner* — Christopher A Hixson
(74) *Attorney, Agent, or Firm* — Brinks Gilson & Lione

(57) ABSTRACT

The present invention is to present a sample analyzer for analyzing a target substance in a sample by carrying out a target substance separating process for separating a complex containing the target substance and a magnetic particle from other substances other than the complex. The sample analyzer executes the target substance separating process with respect to a second container held by a second holder with a second nozzle while executing the target substance separating process with respect to a first container held by a first holder with a first nozzle, and completes the target substance separating process with respect to the first container with the first nozzle and completes the target substance separating process with respect to the second container with the second nozzle.

13 Claims, 16 Drawing Sheets

FIG. 10

| | FIRST TEST (BF PORT 51a) | SECOND TEST (BF PORT 51b) | THIRD TEST (BF PORT 51c) | FOURTH TEST (BF PORT 51d) | FIFTH TEST (BF PORT 51a) |
|---|---|---|---|---|---|
| t1 | TRANSFER TO PRE-MAGNETISM COLLECTING PART | | | | |
| | PRE-MAGNETISM | | | | |
| t2 | | | | | |
| t3 | TRANSFER TO PORT A | | | | |
| t32 | | TRANSFER TO PRE-MAGNETISM COLLECTING PART | | | |
| | ASPIRATING/ DISCHARGING PROCESS (1) | PRE-MAGNETISM | | | |
| t38 | | | | | |
| t4 | | TRANSFER TO PORT B | | | |
| | ASPIRATING/ DISCHARGING PROCESS (2) | ASPIRATING/ DISCHARGING PROCESS (1) | TRANSFER TO PRE-MAGNETISM COLLECTING PART | | |
| | | | PRE-MAGNETISM | | |
| t5 | | | TRANSFER TO PORT C | | |
| | ASPIRATING/ DISCHARGING PROCESS (3) | ASPIRATING/ DISCHARGING PROCESS (2) | ASPIRATING/ DISCHARGING PROCESS (1) | TRANSFER TO PRE-MAGNETISM COLLECTING PART | |
| | | | | PRE-MAGNETISM | |
| t6 | | | | TRANSFER TO PORT D | |
| | ASPIRATING PROCESS | ASPIRATING/ DISCHARGING PROCESS (3) | ASPIRATING/ DISCHARGING PROCESS (2) | ASPIRATING/ DISCHARGING PROCESS (1) | TRANSFER TO PRE-MAGNETISM COLLECTING PART |
| t7 | TRANSFER TO REACTION UNIT | | | | PRE-MAGNETISM |
| | | | | | TRANSFER TO PORT A |
| | | ASPIRATING PROCESS | ASPIRATING/ DISCHARGING PROCESS (3) | ASPIRATING/ DISCHARGING PROCESS (2) | ASPIRATING/ DISCHARGING PROCESS (1) |
| | | TRANSFER TO REACTION UNIT | | | |

FIG. 12

| | FIRST TEST (BF PORT 51a) | | SECOND TEST (BF PORT 51b) | | FIFTH TEST (BF PORT 51a) | |
|---|---|---|---|---|---|---|
| | ASPIRATING/ DISCHARGING PROCESS (3) | COLLECT MAGNETISM | ASPIRATING/ DISCHARGING PROCESS (2) | COLLECT MAGNETISM | | |
| t6 | | COLLECT MAGNETISM | | COLLECT MAGNETISM | | |
| t61 | | ASPIRATE | | ASPIRATE | | |
| t62 | | | | DISCHARGE | | |
| t63 | ASPIRATING PROCESS | COLLECT MAGNETISM | | COLLECT MAGNETISM | | |
| t64 | | | | | TRANSFER TO PRE-MAGNETISM COLLECTING PART | |
| | | ASPIRATE | | ASPIRATE | | |
| t65 | | | | DISCHARGE | | |
| t66 | | COLLECT MAGNETISM | ASPIRATING/ DISCHARGING PROCESS (3) | | | |
| t67 | | MOVE | | MOVE | | |
| | | STIR | | STIR | | |
| t7 | | | | | PRE-MAGNETISM | |
| | TRANSFER TO REACTION UNIT | | | COLLECT MAGNETISM | | |
| t71 | | | | | TRANSFER TO PORT A | |
| | | | ASPIRATING PROCESS | COLLECT MAGNETISM | ASPIRATING/ DISCHARGING PROCESS (1) | COLLECT MAGNETISM |
| | | | | ASPIRATE | | ASPIRATE |
| | | | | | | DISCHARGE |

SAMPLE ANALYZER AND SAMPLE ANALYZING METHOD

RELATED APPLICATIONS

This application claims priority under 35 U.S.C. §119 to Japanese Patent Application No. 2010-278440 filed on Dec. 14, 2010, the entire content of which is hereby incorporated by reference.

BACKGROUND OF THE INVENTION

1. Field of the Invention

The present invention relates to a sample analyzer and a sample analyzing method for analyzing a target substance contained in a sample using a reagent containing magnetic particles.

2. Description of the Related Art

An analyzer for analyzing a target substance contained in a sample using a reagent containing magnetic particles is conventionally known. In such analyzer, the BF (Bound-Free) separating process of separating an immune complex containing the target substance from a unreacted substance is carried out. In the BF separating process, the immune complex in which an analyzing target (antigen or antibody) in the sample and the magnetic particles bound with a reactive substance that specifically binds with the analyzing target are reacted is captured at the inner wall of a reaction container by a magnetic force, and the unreacted substance in the reaction container is removed leaving the immune complex captured at the inner wall of the reaction container by supplying cleaning liquid to the reaction container and aspirating the liquid in the reaction container.

U.S. Patent Publication No. 2008/206099 discloses an analyzer including one magnetism separator, one impurity aspirating mechanism, and one cleaning liquid discharging mechanism, where the BF separating process is carried out by repeating aspiration by the impurity aspirating mechanism and discharge of the cleaning liquid in the reaction container transferred to the magnetism separator.

Japanese Patent Publication No. 2001/91521 discloses an analyzer including a BF separation mechanism with a transferring body for transporting the reaction container, three cleaning ports arranged along the transporting direction of the reaction container by the transferring body, and three BF nozzles, arranged in correspondence with the three cleaning ports, for aspirating the impurities and discharging the cleaning liquid. In such BF separation mechanism, the reaction container is sequentially transported to the three cleaning ports by the transferring body, where the aspiration of the impurities and the discharging of the cleaning liquid are performed two times in each of the three cleaning ports. That is, the BF separating process is completed when the aspiration of the impurities and the discharging of the cleaning liquid are performed for a total of six times on one reaction container when one reaction container passes the three cleaning ports.

However, in the analyzer disclosed in U.S. Patent Publication No. 2008/206099, the BF separating process can be carried out on only one reaction container at once, and hence the BF separating process takes time when processing a great number of reaction containers, and as a result, the sample processing ability of the analyzer becomes difficult to enhance.

Furthermore, in the analyzer disclosed in Japanese Patent Publication No. 2001/91521, the BF nozzle of the cleaning port positioned on the upstream side in the transporting direction of the reaction container is inserted into the specimen of high concentration of the unreacted substance to carry out aspiration and discharge each time, and hence the BF nozzle of the cleaning port on the upstream side is more contaminated than the BF nozzle of the cleaning port on the downstream side. Thus, if only the BF nozzle on the upstream side is cleaned over a long time to prevent occurrence of carry-over of the substance contained in the previous sample to the next sample, the BF separating process cannot be started until the cleaning of the BF nozzle on the upstream side is completed and the sample processing ability of the analyzer becomes difficult to enhance. Furthermore, if the cleaning time is set the same for the BF nozzle on the upstream side and the BF nozzle on the downstream side in view of the processing efficiency, the carry-over to the next sample may occur due to contamination attached to the BF nozzle on the upstream side having high contamination degree.

SUMMARY OF THE INVENTION

The scope of the present invention is defined solely by the appended claims, and is not affected to any degree by the statements within this summary.

A first aspect of the present invention is a sample analyzer for analyzing a target substance in a sample by carrying out a target substance separating process for separating a complex containing the target substance and a magnetic particle from other substances other than the complex, the sample analyzer comprising: a first holder for holding a first container accommodating a liquid specimen containing a target substance and magnetic particles; a first magnet for magnetically capturing the magnetic particles in the first container held by the first holder; a first nozzle for discharging a cleaning liquid into the first container held by the first holder and aspirating a liquid in the first container; a second holder for holding a second container accommodating a liquid specimen containing a target substance and magnetic particles; a second magnet for magnetically capturing the magnetic particles in the second container held by the second holder; a second nozzle for discharging a cleaning liquid into the second container held by the second holder and aspirating a liquid in the second container; a container transfer unit for transferring a container to the first holder or the second holder; and a controller for executing the target substance separating process with respect to the second container held by the second holder with the second nozzle while executing the target substance separating process with respect to the first container held by the first holder with the first nozzle, and for completing the target substance separating process with respect to the first container with the first nozzle and completing the target substance separating process with respect to the second container with the second nozzle, wherein in the target substance separating process with respect to the first container, a discharging/aspirating process including the discharge of the cleaning liquid into the first container and the aspiration of the liquid in the first container is carried out over plural number of times with the first nozzle; and in the target substance separating process with respect to the second container, a discharging/aspirating process including the discharge of the cleaning liquid into the second container and the aspiration of the liquid in the second container is carried out over plural number of times with the second nozzle.

A second aspect of the present invention is a sample analyzing method of analyzing a target substance in a sample by carrying out a target substance separating process for separating a complex containing the target substance and a magnetic particle from other substances other than the complex, the sample analyzing method comprising steps of (a) transferring a first container accommodating a liquid specimen containing a target substance and magnetic particles to a first holder; (b) transferring a second container accommodating a liquid specimen containing a target substance and magnetic particles to a second holder; (c) executing the target substance separating process with respect to the second container held by the second holder with a second nozzle while executing the target substance separating process with respect to the first container held by the first holder with a first nozzle, and completing the target substance separating process with respect to the first container with the first nozzle and completing the target substance separating process with respect to the second container with the second nozzle, wherein in the target substance separating process with respect to the first container, a discharging/aspirating process including a discharge of a cleaning liquid into the first container and an aspiration of a liquid in the first container is carried out over plural number of times with the first nozzle, and in the target substance separating process with respect to the second container, a discharging/aspirating process including a discharge of a cleaning liquid into the second container and an aspiration of a liquid in the second container is carried out over plural number of times with the second nozzle.

BRIEF DESCRIPTION OF THE DRAWINGS

FIG. 10 is a timing chart for describing the BF separating process by the primary BF separator of the immune analyzer according to one embodiment of the present invention;

FIG. 12 is a timing chart for describing a BF cleaning process (aspirating process) in the BF separating process shown in FIG. 10;

DETAILED DESCRIPTION OF THE PREFERRED EMBODIMENT

Hereinafter embodiments embodying the present invention will be described based on the drawings.

First, the configuration of an immune analyzer 1 according to one embodiment of the present invention will be described with reference to FIGS. 1 to 9.

The immune analyzer 1 according to one embodiment of the present invention is an apparatus for quantitatively measuring or qualitatively measuring antigens and antibodies contained in a sample (blood specimen) such as blood to be measured. The immune analyzer 1 is configured to bind magnetic particles (R2 reagent) to a capture antibody (R1 reagent) bound to an antigen contained in a sample (blood serum), and thereafter, capture a complex of the bound antigen, capture antibody, and magnetic particles by magnetism of a primary BF separator 11 to remove (BF separation) the R1 reagent containing unreacted (free) capture antibody. The immune analyzer 1 binds the antigen bound with the magnetic particles and a labeled antibody (R3 reagent), and thereafter, captures a complex of the bound magnetic particles, antigen, and labeled antibody by magnetism of a secondary BF separator 12 to remove (BF separation) the R3 reagent containing unreacted (free) labeled antibody. The immune analyzer 1 also adds a dispersion liquid (R4 reagent) and a light emitting substrate (R5 reagent) that emits light in the reaction process with the labeled antibody, and then measures the light emitting amount generated by the reaction of the labeled antibody and the light emitting substrate. The immune analyzer 1 quantitatively measures the antigen contained in the sample that binds with the labeled antibody through such steps. The immune analyzer 1 is configured to be able to perform analysis corresponding to a plurality of different analyzing items with respect to the sample.

Figure 1:
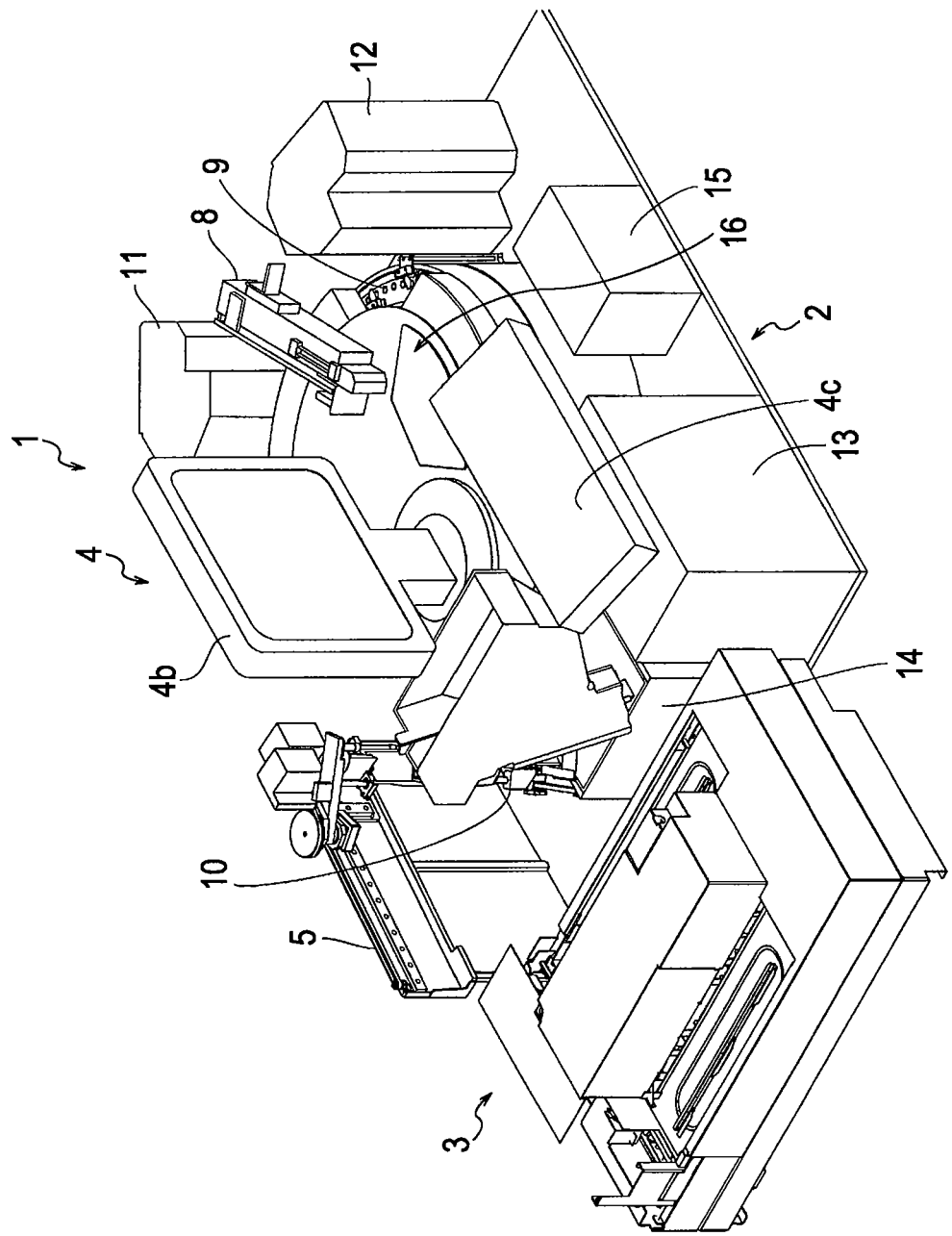
FIG. 1 is a perspective view showing an overall configuration of an immune analyzer according to one embodiment of the present invention.
Figure 2:
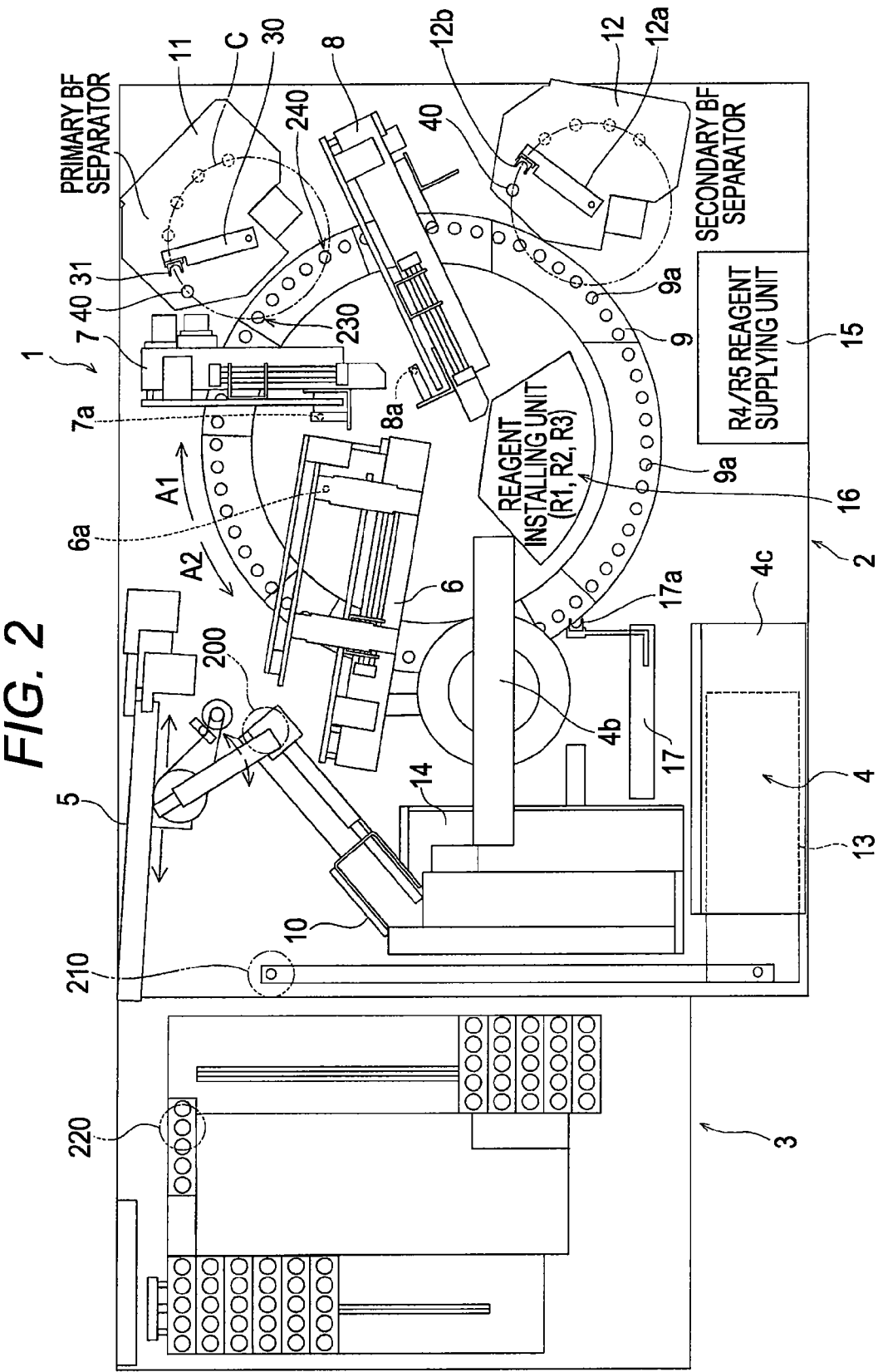
FIG. 2 is a plan view showing an overall configuration of the immune analyzer according to one embodiment of the present invention.

As shown in FIG. 1 and FIG. 2, the immune analyzer 1 includes a measurement mechanism section 2, a sample transporting section (sampler) 3 arranged to be adjacent to the measurement mechanism section 2, and a control device 4 including a PC (personal computer) electrically connected to the measurement mechanism section 2.

The sample transporting section 3 is configured to transport a rack mounted with a plurality of test tubes accommodating the sample. The sample transporting section 3 has a function of transporting the test tube accommodating the sample to a sample aspirating position 220 by a sample dispensing arm 5.

Figure 3:
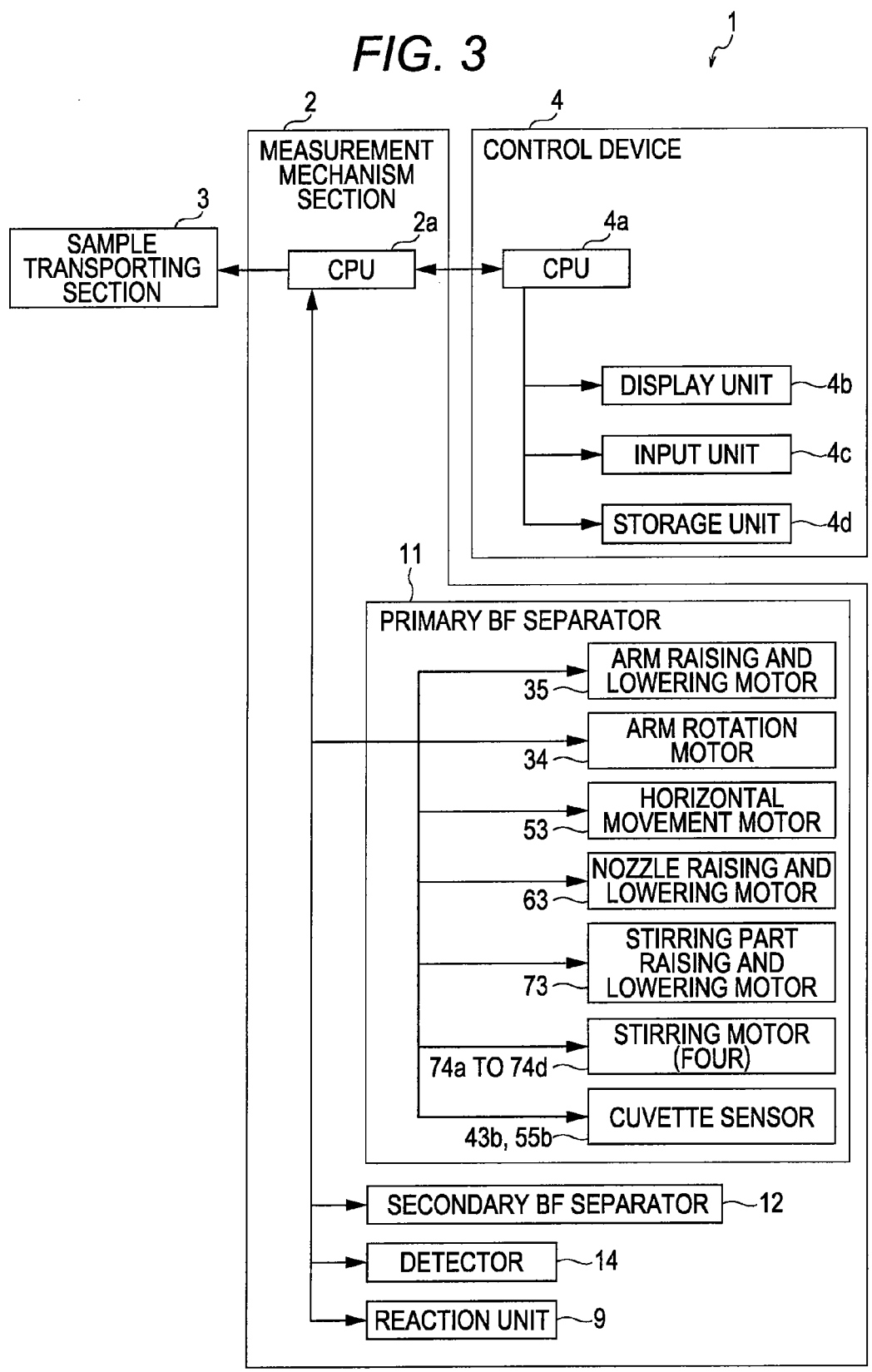
FIG. 3 is a block diagram for describing the configuration of the immune analyzer according to one embodiment of the present invention.

As shown in FIG. 3, the control device 4 includes a CPU 4a, a display unit 4b, an input unit 4c, and a storage unit 4d. The CPU 4a has a function of analyzing the measurement result obtained by the measurement mechanism section 2, and displaying the analysis result on the display unit 4b. The storage unit 4d includes an HDD (Hard Disc Drive), and is configured to store various types of programs and data of measurement results, and the like.

As shown in FIG. 2, the measurement mechanism section 2 is configured by a sample dispensing arm 5, an R1 reagent dispensing arm 6, a R2 reagent dispensing arm 7, a R3 reagent dispensing arm 8, reaction unit 9, a cuvette supplying unit 10, the primary BF separator 11, the secondary BF separator 12, a pipette tip supplying unit 13, a detector 14, a R4/R5 reagent supplying unit 15, and a reagent installing unit 16.

As shown in FIG. 3, each mechanism unit (reaction unit 9, primary BF separator 11, etc.) in the measurement mechanism section 2 is controlled by a CPU 2a arranged in the measurement mechanism section 2. The CPU 2a is communicably connected to the sample transporting section 3 and the control device 4, and has a function of receiving an operation command from the control device, transmitting measurement result data to the control device 4, transmitting an operation command to the sample transporting section 3, and the like.

Figure 7:
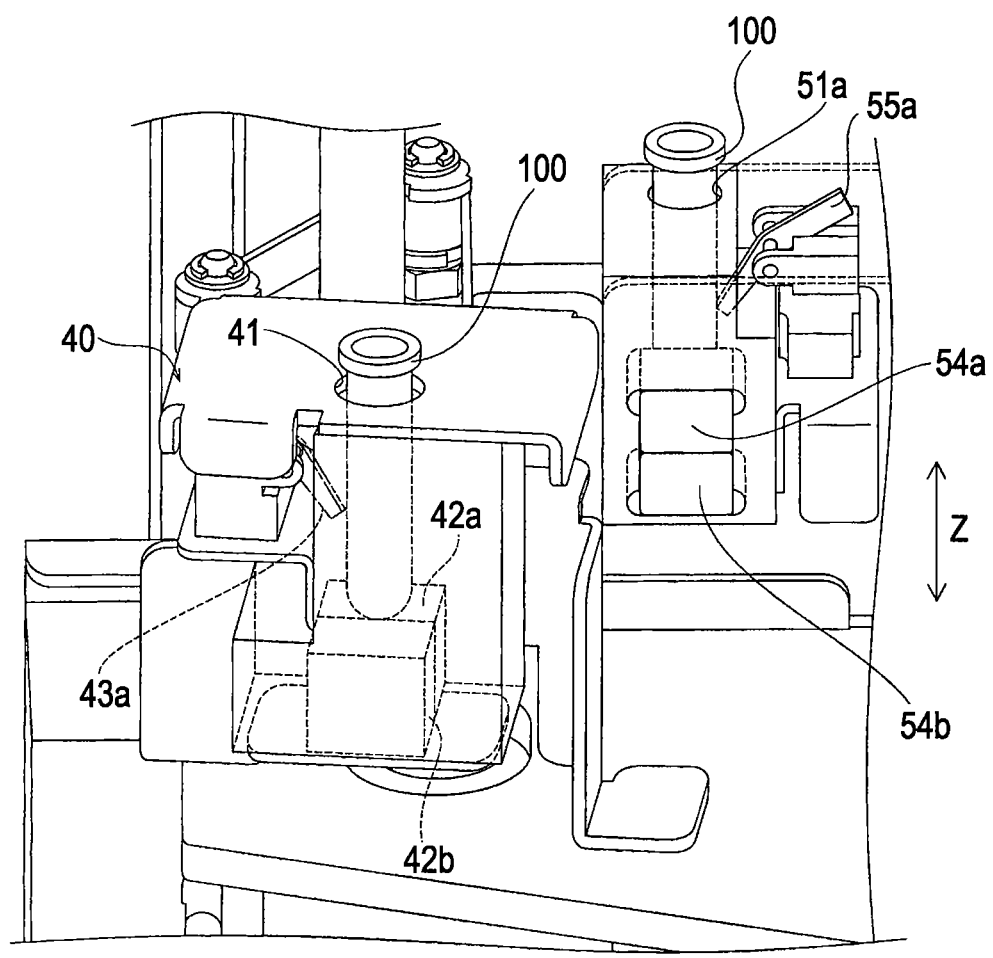
FIG. 7 is a perspective view for describing the pre-magnetism collecting part and the BF ports of the primary BF separator shown in FIG. 4.

The cuvette supplying unit 10 shown in FIG. 2 is configured to accommodate a plurality of cuvettes 100 (see FIG. 7), and has a function of sequentially supplying the cuvette one by one to a sample discharging position 200 by the sample dispensing arm 5. As shown in FIG. 7, the cuvette 100 is an elongate cylindrical container that has an opened upper end and a bottom which lower end is rounded, where the inner side surface and the outer side surface are formed to a circular shape in the horizontal cross-section. The cuvette 100 is formed with a projection that projects out to the outer side from the outer side surface of the upper end so as to be gripped by a catcher arranged at each area of the measurement mechanism section 2.

As shown in FIG. 2, the R1 reagent dispensing arm 6 is configured to aspirate the R1 reagent with a pipette 6a from the R1 reagent container installed in the reagent installing unit 16, and dispense (discharge) the aspirated R1 reagent to the cuvette 100 mounted at the sample discharging position 200. The R1 reagent dispensing arm 6 also has a function of transferring the cuvette 100 mounted at the sample discharging position 200 to the reaction unit 9 by means of the catcher.

The pipette tip supplying unit 13 has a function of transporting the plurality of input pipette tips one by one to a tip attaching position 210 by means of the sample dispensing arm 5.

The sample dispensing arm 5 is configured to be movable, and has a function of aspirating the sample in the test tube transported to the sample aspirating position 220 by the sample transporting section 3, and dispensing (discharging) the sample into the cuvette at the sample discharging position 200, to which the R1 reagent is dispensed by the R1 reagent dispensing arm 6, after attaching the pipette tip at the tip attaching position 210.

The R2 reagent dispensing arm 7 is configured to aspirate the R2 reagent with a pipette 7a from the R2 reagent container installed in the reagent installing unit 16, and dispense (discharge) the aspirated R2 reagent to the cuvette 100 accommodating the R1 reagent and the sample.

The reaction unit 9 is formed to a substantially circular ring shape so as to surround the periphery of the reagent installing unit 16 having a substantially circular shape when seen in plan view. The reaction unit 9 is configured to be rotatable, and has a function of moving the cuvette 100 held by a cuvette holder 9a to each processing position where various types of processes (dispensing of reagent, etc.) are carried out. Specifically, the reaction unit 9 rotates in the direction of the arrow A1 to transport the cuvette 100 transferred to the reaction unit 9 by the R1 reagent dispensing arm 6 to each processing position of the R2 reagent dispensing arm 7, the primary BF separator 11, the R3 reagent dispensing arm 8, the secondary BF separator 12, and the R4/R5 reagent supplying unit 15 in such order, and then transfers the same to the detector 14.

The primary BF separator 11 is configured to take out the cuvette 100 accommodating the sample, the R1 reagent, and the R2 reagent from the reaction unit 9 by means of a catcher 31 of a transfer arm 30, and separate (BF separation) the unreacted R1 reagent (unnecessary component) and the magnetic particles from the specimen in the cuvette 100. After the BF separating process is completed, the primary BF separator 11 returns the cuvette 100 to the reaction unit 9 by means of the catcher 31 of the transfer arm 30. The structure of the primary BF separator 11 will be described in detail later.

The R3 reagent dispensing arm 8 is configured to aspirate the R3 reagent with a pipette 8a from the R3 reagent container installed in the reagent installing unit 16. The R3 reagent dispensing arm 8 is configured to dispense (discharge) the aspirated R3 reagent to the cuvette 100 accommodating the specimen after the BF separation by the primary BF separator 11.

The secondary BF separator 12 is configured to acquire the cuvette 100 accommodating the specimen and the R3 reagent of after the BF separation by the primary BF separator 11 from the reaction unit 9 with a catcher 12b of the transfer arm 12a, and separate (BF separation) the unreacted R3 reagent (unnecessary component) and the magnetic particles from the specimen in the cuvette. Thereafter, the secondary BF separator 12 is configured to return the cuvette 100 to the reaction unit 9 with the catcher 12b of the transfer arm 12a.

The R4/R5 reagent supplying unit 15 is configured to dispense the R4 reagent and the R5 reagent to the cuvette 100 accommodating the specimen after the BF separation by the secondary BF separator 12 with a tube.

The detector 14 is arranged to measure the amount of antigen contained in a sample by obtaining the light generated in the reaction process of the labeled antibody bound to the antigen of the sample performed with a predetermined process and the light emitting substrate with a photo multiplier tube. The cuvette 100 is taken out from the reaction unit 9 by a cuvette transferring unit 17 including a catcher 17a and set in the detector 14. The cuvette transferring unit 17 also has a function of taking out the cuvette 100 of after the measurement by the detector 14 is finished from the detector 14 and discarding the same in a discarding unit, other than transferring the cuvette 100 to the detector 14.

The reagent installing unit 16 is arranged to install the R1 reagent container accommodating the R1 reagent containing the capture antibody, the R2 reagent container accommodating the R2 reagent containing the magnetic particles, and the R3 reagent container accommodating the R3 reagent containing the labeled antibody respectively in plurals.

The configuration of the primary BF separator 11 will now be described in detail. The configuration of the secondary BF separator 12 is similar to the primary BF separator 11, and thus the description thereof will be omitted.

Figure 4:
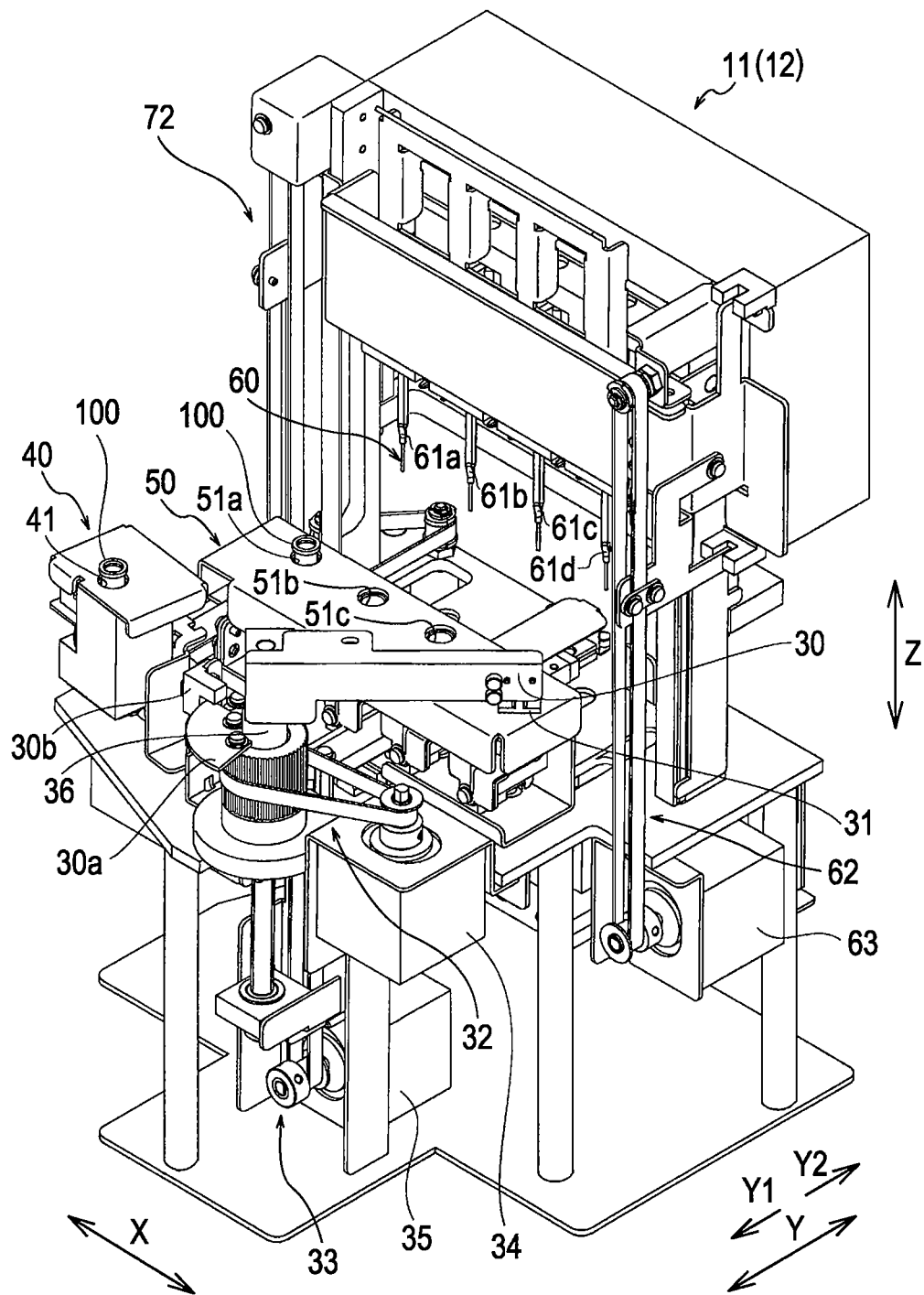
FIG. 4 is a perspective view for describing a configuration of a primary BF separator of the immune analyzer according to one embodiment of the present invention.
Figure 5:
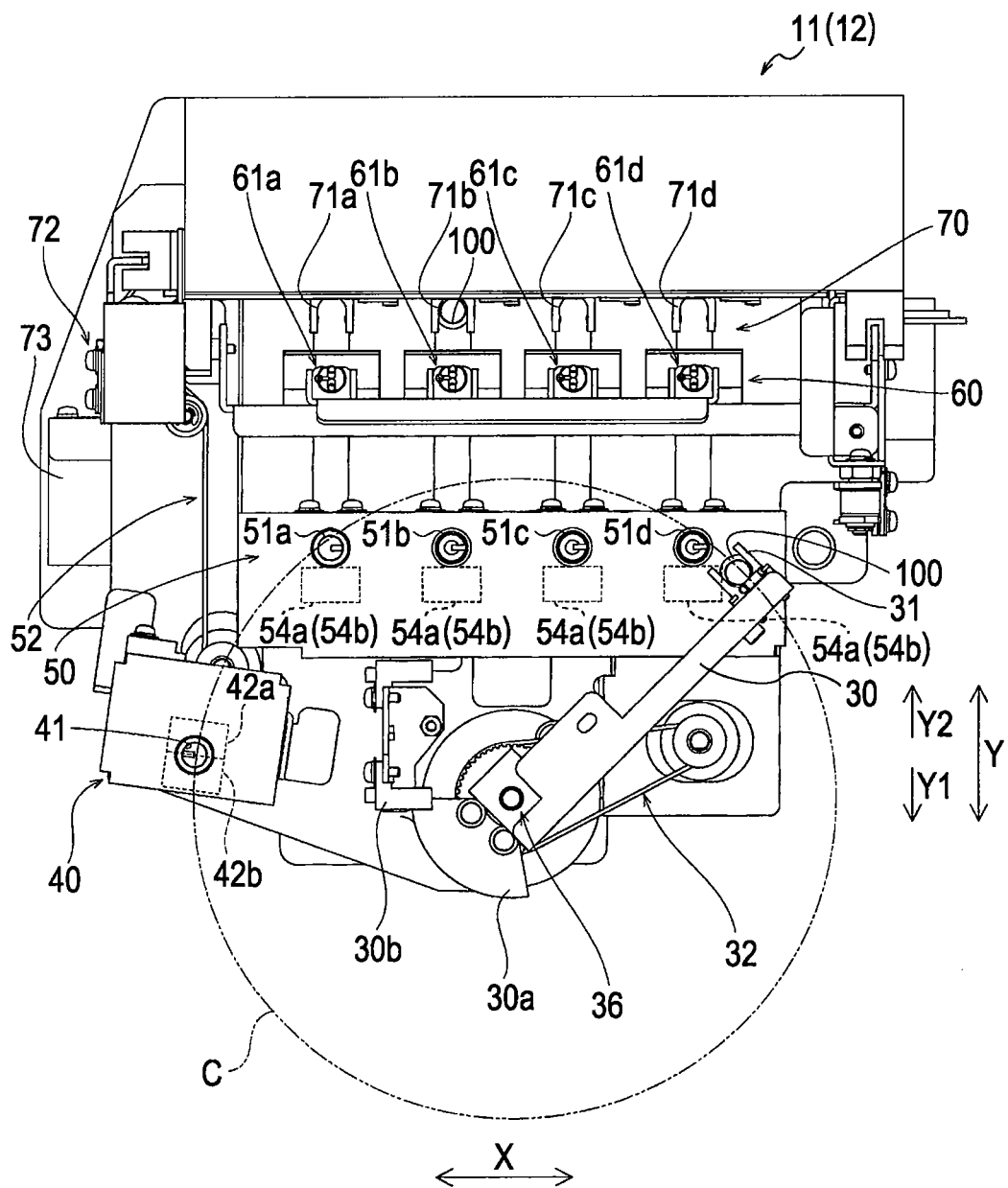
FIG. 5 is a plan view of the primary BF separator shown in FIG. 4.
Figure 6:
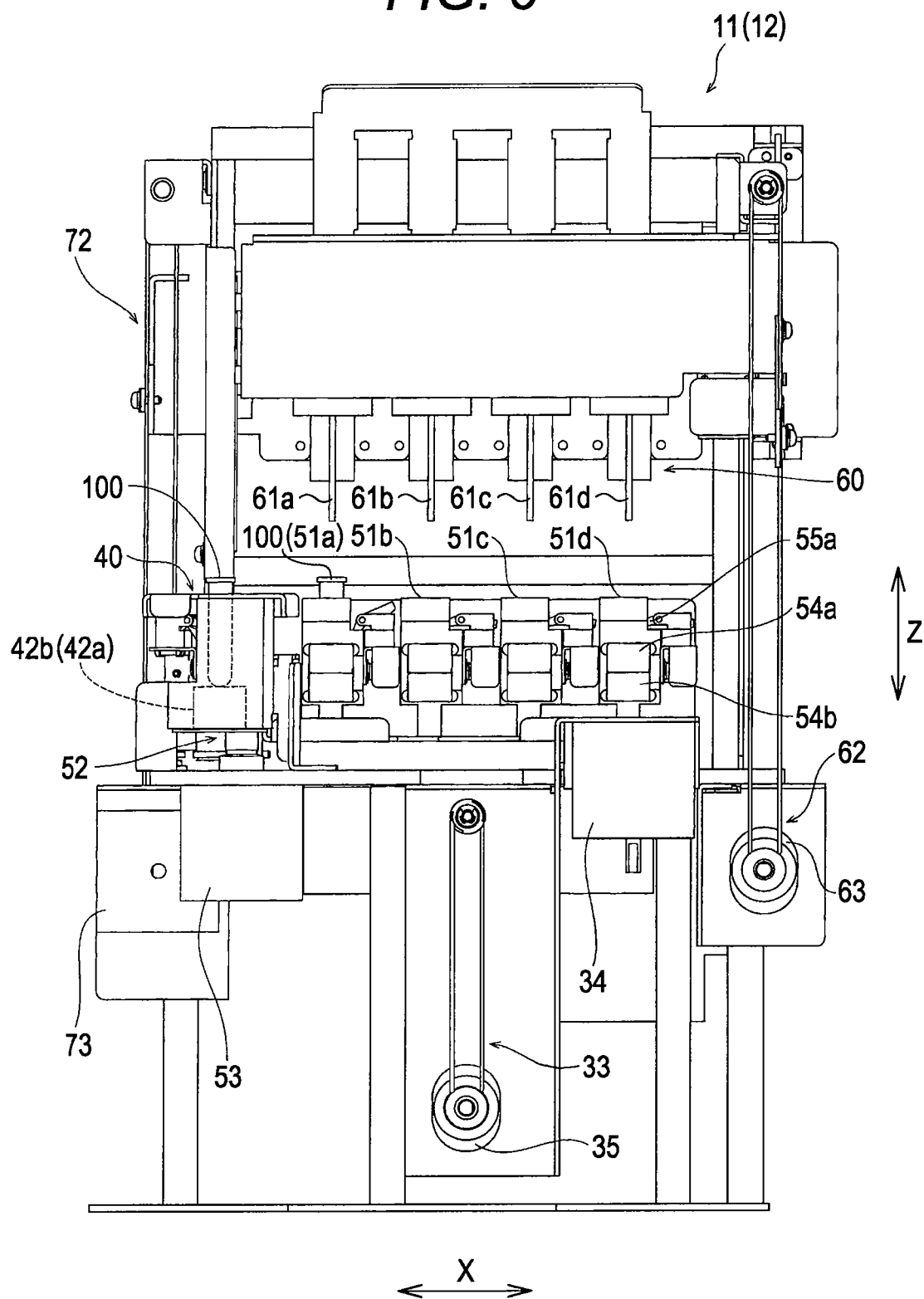
FIG. 6 is a schematic view showing a pre-magnetism collecting part and BF ports of the primary BF separator shown in FIG. 4 from a front surface side.

As shown in FIG. 4 to FIG. 6, the primary BF separator 11 mainly includes a transfer arm 30 with a catcher 31 for taking out the cuvette 100, a pre-magnetism collecting part 40, a movable installing part 50, a nozzle part 60, and a stirring part 70 (see FIG. 5). The movable installing part 50 includes four BF ports 51a to 51d (see FIG. 5) arranged side by side to install the cuvette 100 accommodating the sample, the R1 reagent, and the R2 reagent, and to carry out the BF separating process. The nozzle part 60 includes four nozzles 61a to 61d (see FIG. 6) corresponding to the four BF ports 51a to 51d. The stirring part 70 includes four stirring catchers 71a to 71d (see FIG. 5) corresponding to the four BF ports 51a to 51d. Thus, in the primary BF separator 11, the BF separating process can be carried out in parallel with respect to a maximum of four cuvettes 100 (specimen in cuvette 100) installed in each of the four BF ports 51a to 51d. In FIG. 6, a state in which the transfer arm 30 and the upper cover and the like of the movable installing part 50 are removed is schematically shown to show the structure of the BF ports 51a to 51d.

As shown in FIG. 5, the transfer arm 30 includes the catcher 31 for gripping the cuvette 100 at the distal end, and has a function of transferring the cuvette 100 among the pre-magnetism collecting part 40, the four BF ports 51a to 51d of the movable installing part 50, and the cuvette holder 9a (see FIG. 2) of the reaction unit 9. Specifically, as shown in FIG. 4, the transfer arm 30 is configured to be able to turn (pivot) with a rotation shaft 36 extending in the up and down direction (Z direction) as a center and to be able to rise and lower in the up and down direction (Z direction) by an arm rotation motor 34 and an arm raising and lowering motor 35 connected through transmission mechanisms 32 and 33 including a belt and a pulley. The catcher 31 thus moves on a predetermined arcuate trajectory C (see FIG. 5) that passes through a cuvette installing portion 41, to be described later, of the pre-magnetism collecting part 40, the BF ports 51a to 51d, and the cuvette holder 9a (take-out position 230 and return position 240, see FIG. 2), thus enabling the installing and the take-out of the cuvette 100 at each part. The transfer arm 30 includes a detection plate 30a that integrally rotates with the rotation shaft 36, where the detection plate 30a can be detected by a light transmissive sensor 30b. The origin setting of the pivoting direction of the transfer arm 30 is carried out based on the detection result of the sensor 30b.

Figure 8:
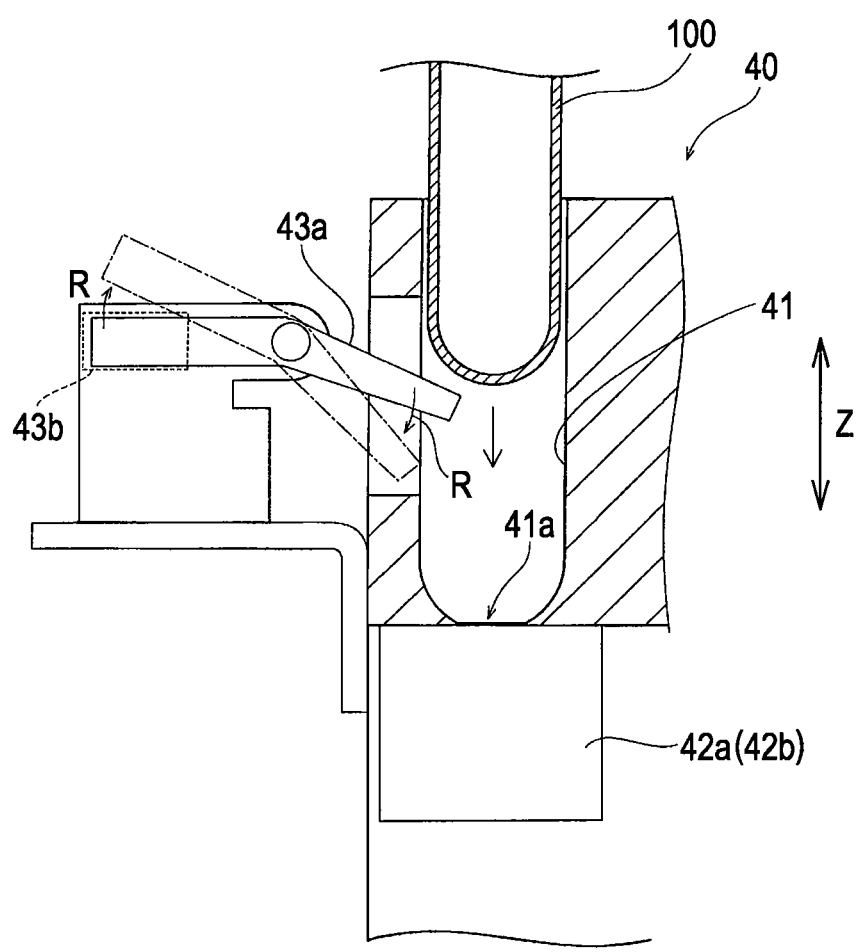
FIG. 8 is a cross-sectional view schematically showing an internal structure of the pre-magnetism collecting part of the primary BF separator shown in FIG. 4.

The pre-magnetism collecting part 40 has a function of capturing the magnetic particles in the cuvette 100 in advance prior to the BF separating process carried out in each BF port 51a to 51d of the movable installing part 50. The pre-magnetism collecting part 40 includes one cuvette installing portion 41 arranged on the arcuate trajectory C of the transfer arm 30 (catcher 31) at the position on the near side (direction of arrow Y1) of the primary BF separator 11. As shown in FIG. 8, the cuvette installing portion 41 is configured to be able to arrange the cuvette 100 accommodating the sample, the R1 reagent, and the R2 reagent, and includes a hole having a shape corresponding to the outer shape of the cuvette 100. As shown in FIG. 7, the pre-magnetism collecting part 40 incorporates two in a set of permanent magnets 42a and 42b having a rectangular solid shape to magnetically capture the magnetic particles in the cuvette 100.

As shown in FIG. 5, the permanent magnets 42a and 42b are arranged to overlap the cuvette 100 set in the cuvette installing portion 41 when seen in plan view. More specifically, as shown in FIG. 7, the permanent magnets 42a and 42b are arranged at positions immediately below the cuvette 100 set in the cuvette installing portion 41, and are configured to magnetically capture (magnetism collect) the magnetic particles in the cuvette 100 from the lower side at such positions. The bottom of the cuvette installing portion 41 is formed to a curved surface that narrows in accordance with the shape of the bottom of the cuvette 100, and is formed with an opening 41a (see FIG. 8) to expose the bottom of the set cuvette 100. The permanent magnets 42a and 42b are arranged at positions to be brought into contact with the bottom (outer bottom surface) of the cuvette 100 exposed from the opening 41a of the cuvette installing portion 41 when the cuvette 100 is set in the cuvette installing portion 41. The magnets 42a and 42b may be arranged at positions slightly spaced apart from the bottom (outer bottom surface) of the cuvette 100 exposed from the opening 41a of the cuvette installing portion 41.

Figure 9:
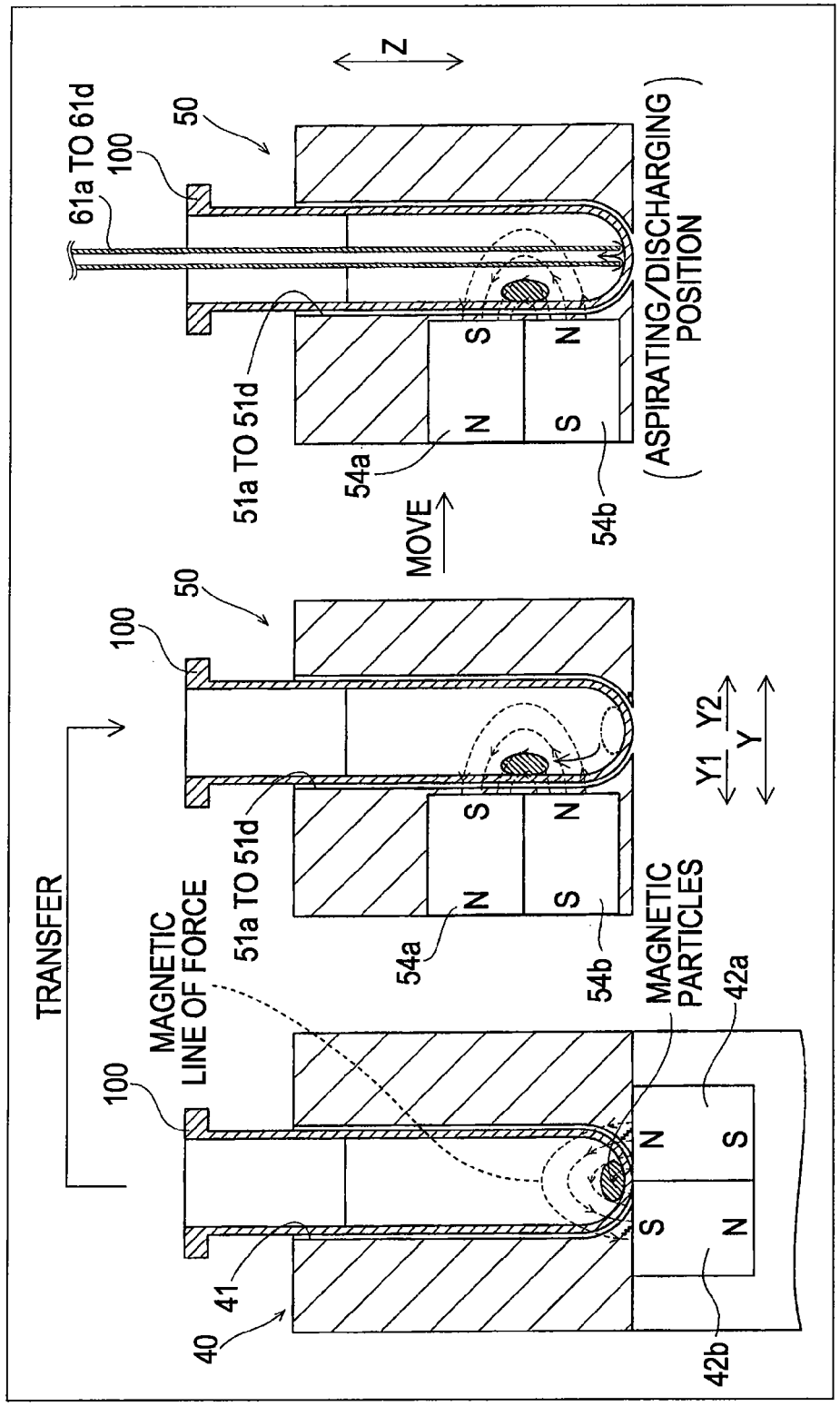
FIG. 9 is a schematic view for describing the functions of the pre-magnetism collecting part and the BF ports of the primary BF separator shown in FIG. 4.

As shown in FIG. 9, the two in a set of permanent magnets 42a and 42b are arranged next to each other horizontally, and are installed such that the upper surface side of one permanent magnet 42a becomes the N pole (lower surface side is the S pole), and the upper surface side of the other permanent magnet 42b becomes the S pole (lower surface side is the N pole). The intermediate position (on boundary line) of the two in a set of permanent magnets 42a and 42b arranged horizontally thus has the strongest magnetic force. The permanent magnets 42a and 42b are arranged such that the intermediate part, where the magnetic force is the strongest, is positioned immediately below the lower end of the cuvette 100 set in the cuvette installing portion 41. The magnetic particles in the cuvette 100 are thus reliably captured at the inner bottom surface (lowest position) of the cuvette 100. The pre-magnetism collecting part 40 is made of non-magnetic aluminum (alloy), so that the magnetic line of force (see FIG. 9) by the permanent magnets 42a and 42b passes through without barely being inhibited by the peripheral wall surrounding the cuvette 100 and reaches the cuvette 100.

As shown in FIG. 8, a detection piece 43a that can advance to the inside of the cuvette installing portion 41 and retreat from the inside, and a light transmissive cuvette sensor 43b (see broken line in FIG. 8) for detecting the detection piece 43a are arranged on the side surface side of the cuvette installing portion 41. The detection piece 43a light shields the cuvette sensor 43b if the cuvette 100 is not set. The detection piece 43a turns in the direction of the arrow R with the setting of the cuvette 100 in the cuvette installing portion 41, so that the light shielding by the detection piece 43a can be released (see chain dashed line in FIG. 8). Thus, it is configured to be capable of detecting whether or not the cuvette 100 is set in the pre-magnetism collecting part 40 (cuvette installing portion 41).

As shown in FIG. 5, the movable installing part 50 includes four BF ports 51a to 51d arranged at equal interval in a straight line in the horizontal direction (X direction). The movable installing part 50 is configured to be horizontally movable in the Y direction by the horizontal movement motor 53 (see FIG. 6) connected through the transmission mechanism 52 including the belt and the pulley. Therefore, the movable installing part 50 has a function of arranging each of the four BF ports 51a to 51d to the position (cuvette setting position) on the arcuate trajectory C of the transfer arm 30 (catcher 31), the position (aspirating/discharging position) immediately below the nozzle 61a to 61d corresponding to each BF port 51a to 51d, and the cuvette take-out position of the stirring catcher 71a to 71d corresponding to each BF port 51a to 51d. As apparent from FIG. 5, the position (cuvette setting position) where each BF port 51a to 51d that moves in the Y direction intersects the arcuate trajectory C differs from each other with respect to the Y direction. Thus, the movable installing part 50 is controlled to change the movement position in the Y direction depending on which of the BF ports 51a to 51d to set the cuvette 100 transferred from the transfer arm 30.

As shown in FIG. 6, each BF port 51a to 51d of the movable installing part 50 has the same structure, and includes a hole in which the cuvette 100 can be arranged. Each BF port 51a to 51d includes two in a set of permanent magnets 54a and 54b having a rectangular solid shape, and is configured to capture the magnetic particles in the cuvette 100 installed in the BF port 51a to 51d. The permanent magnets 54a and 54b of the BF port 51a to 51d are arranged to be positioned at the side of the set cuvette 100, as opposed to the permanent magnets 42a and 42b of the pre-magnetism collecting part 40. Specifically, as shown in FIG. 5 and FIG. 7, the permanent magnets 54a and 54b are arranged at the positions on the side on the near side (direction of arrow Y1) of the cuvette 100 installed in the BF port 51a to 51d.

As shown in FIG. 9, the two in a set of permanent magnets 54a and 54b are arranged next to each other vertically, and are installed such that the side surface side on the cuvette 100 side (direction of arrow Y2) of the upper permanent magnet 54a becomes the S pole (direction of arrow Y1 is the N pole), and the side surface side on the cuvette 100 side (direction of arrow Y2) of the lower permanent magnet 54b becomes the N pole (direction of arrow Y1 is the S pole). The position of intermediate height (on boundary line) of the two in a set of permanent magnets 54a and 54b arranged vertically thus has the strongest magnetic force. Therefore, the magnetic particles in the cuvette 100 installed in the BF port 51a to 51d are captured at the inner side surface at the height position on the upper side than the inner bottom surface by the permanent magnets 54a and 54b.

In the BF separating process, the cuvette 100 in which the magnetic particles are captured in advance by the pre-magnetism collecting part 40 is taken out from the pre-magnetism collecting part 40 by the transfer arm 30 (catcher 31), and transferred to one of the four BF ports 51a to 51d. Thus, when the cuvette 100 is installed at one of the BF ports 51a to 51d, the magnetic particles in the cuvette 100 are already collected in a lump at the inner bottom surface side of the cuvette 100. When the cuvette 100 is installed in one of the BF ports 51a to 51d, the lump of magnetic particles collected at the inner bottom surface of the cuvette 100 moves to the capturing position of the inner side surface on the upper side along the inner wall of the cuvette 100 in the lump state by the magnetic force of the permanent magnets 54a and 54b at the side. The magnetic force is not applied on the magnetic particles in the cuvette 100 from when the cuvette 100 is taken out by the transfer arm 30 in the pre-magnetism collecting part 40 until the cuvette 100 is set in one of the BF ports 51a to 51d, but the magnetic particles in the cuvette 100 maintain the state collected at the inner bottom surface of the cuvette 100 by the own weight of the magnetic particles. Thus, the magnetic particles can be rapidly captured in the BF port 51a to 51d even if the magnetic force is not continuously applied on the magnetic particles when the cuvette 100 is being transferred.

As shown in FIG. 5, the transfer arm 30 has a structure of pivoting about the rotation shaft 36, and hence the cuvettes 100 to be set in the four BF ports 51a to 51d are set in different directions according to the rotation angle of the transfer arm 30 when seen in plan view. In the present embodiment, the magnetic particles are captured at the inner bottom surface of the cuvette 100 in the pre-magnetism collecting part 40, and the magnetic particles are captured at the inner side surface of the cuvette 100 having a circular shape in horizontal cross-section in each BF port 51a to 51d. Thus, the BF separating process can be carried out with the magnetic particles captured in the same exact manner in each BF port 51a to 51d even if the direction of the cuvette 100 of when set in each BF port 51a to 51d differs according to the rotation angle of the transfer arm 30.

As shown in FIG. 7, each BF port 51a to 51d of the movable installing part 50 also includes a detection piece 55a, and a light transmissive cuvette sensor 55b (see FIG. 3) for detecting the detection piece 55a similar to the pre-magnetism collecting part 40. Thus, whether or not the cuvette 100 is set in each of the four BF ports 51a to 51d can be detected.

As shown in FIG. 5, the nozzle part 60 includes four nozzles 61a to 61d arranged at equal interval in a straight line in the horizontal direction (X direction) in correspondence with the four BF ports 51a to 51d. As shown in FIG. 4, the nozzle part 60 is configured to be able to rise and lower in the up and down direction (Z direction) by a nozzle raising and lowering motor 63 connected through a transmission mechanism 62 including a belt and a pulley. Therefore, the four nozzles 61a to 61d integrally rise and lower by one nozzle raising and lowering motor 63 of the nozzle part 60. The nozzle part 60 thus has a function of advancing (lowering) the four nozzles 61a to 61d to inside the cuvette 100 set in the four BF ports 51a to 51d or retreating (raising) the four nozzles 61a to 61d from inside the cuvette 100 while being arranged at the position (aspirating/discharging position) immediately below each nozzle 61a to 61d, to which the four BF ports 51a to 51d correspond, by the movement of the movable installing part 50.

The four nozzles 61a to 61d have the same structure, and have a structure in which three nozzles, a discharging nozzle for discharging the cleaning liquid, an aspirating nozzle for aspirating the liquid (unreacted substance) in the cuvette 100, and a cleaning nozzle for discharging the cleaning liquid for cleaning the discharging nozzle and the aspirating nozzle, form a set. The cleaning port is arranged at the position on the lower side of the four nozzles 61a to 61d, respectively, so that the nozzles 61a to 61d themselves can be cleaned. The aspiration and discharge of the four nozzles 61a to 61d can be individually operated, where control is performed such that the aspirating and discharging operation of the corresponding nozzle 61a to 61d is not carried out when the cuvette 100 is not set in one of the four BF ports 51a to 51d.

Furthermore, as shown in FIG. 9, when aspirating the liquid (unreacted substance) in the cuvette 100 with the nozzles 61a to 61d, such aspiration is carried out with the distal end of the nozzle (aspirating nozzle) 61a to 61d lowered to the vicinity of the bottom (inner bottom surface) of the cuvette 100. The magnetic particles can be suppressed from being aspirated when aspirating the liquid (unreacted substance) since the magnetic particles are captured on the inner side surface side spaced apart to the upper side from the bottom of the cuvette 100 in the BF ports 51a to 51d.

As shown in FIG. 5, the stirring part 70 includes four stirring catchers 71a to 71d arranged at equal interval in a straight line in the horizontal direction (X direction) in correspondence with the four BF ports 51a to 51d. As shown in FIG. 6, the stirring part 70 is configured to be able to rise and lower in the up and down direction (Z direction) by a stirring part raising and lowering motor 73 connected through a transmission mechanism 72 including a belt and a pulley. Thus, the four stirring catchers 71a to 71d integrally rise and fall by one stirring part raising and lowering motor 73 of the stirring part 70. Thus, the stirring part 70 has a function of causing the corresponding stirring catchers 71a to 71d to grip the cuvettes 100 of the four BF ports 51a to 51d by lowering such that the stirring catchers 71a to 71d are arranged at the cuvette take-out positions at where the cuvette 100 set in each BF port 51a to 51d can be gripped. The stirring part 70 can also take out the cuvette 100 from the BF port 51a to 51d, and return the cuvette 100 taken out to each BF port 51a to 51d by rising or lowering while gripping the cuvette of each BF port 51a to 51d with the corresponding stirring catcher 71a to 71d.

The four stirring catchers 71a to 71d each includes a stirring motor 74a to 74d (see FIG. 3) for oscillating (vibrating) the stirring catcher 71a to 71d. The stirring catchers 71a to 71d have a function of stirring the magnetic particles inside the cuvette 100 by driving the stirring motor 74a to 74d while gripping the cuvette 100 and taking out the same from the BF port 51a to 51d (state in which the magnetic particles are not captured by the permanent magnets 54a and 54b). The unreacted substance and the like sandwiched between the magnetic particles captured to a lump thus can be dispersed. The stirring motors 74a to 74d arranged in the four stirring catchers 71a to 71d can be individually driven. Thus, control can be made not to carry out the stirring operation by the corresponding stirring catcher 71a to 71d when the cuvette 100 is not set in one of the four BF ports 51a to 51d.

According to the above configuration, in the primary BF separator 11, the BF separating process can be individually carried out by the corresponding nozzle 61a to 61d and the stirring catcher 71a to 71d in each of the four BF ports 51a to 51d. In the BF separating process, the operation of aspirating (removing) the liquid in the cuvette 100 with the corresponding nozzle 61a to 61d with the magnetic particles captured in the BF port 51a to 51d, the operation of discharging the cleaning liquid into the cuvette 100 with the corresponding nozzle 61a to 61d, and the operation of stirring the specimen in the cuvette 100 with the corresponding stirring catcher 71a to 71d are repeatedly carried out over plural times. The concentration of the unreacted substance inside the cuvette 100 thus can be lowered in a step-wise manner while leaving the magnetic particles, so that the complex of the magnetic particles, the antigen, and the capture antibody, and the unreacted substance can be separated (BF separation).

As shown in FIG. 2, in the present embodiment, all the cuvettes 100 supplied to the BF separating process pass through the same transport path (transport path by reaction unit 9 and transfer arm 30) until transferred to the pre-magnetism collecting part 40. Each cuvette 100 is transferred to a different transport path when being transferred to either one of the BF ports 51a to 51d from the pre-magnetism collecting part 40.

The BF separating processing operation of the primary BF separator 11 of the immune analyzer 1 (measurement mechanism section 2) according to one embodiment of the present invention will now be described with reference to FIG. 2, FIG. 3, FIG. 5, and FIG. 9 to FIG. 12. The BF separating processing operation by the primary BF separator 11 operates at a predetermined timing set in advance according to the timing chart shown in FIG. 10 to synchronize with the dispensing operation by various dispensing arms and the transportation of the cuvette 100 by the reaction unit 9 as one part of the measurement processing operation of the entire immune analyzer 1. The BF separating process by the primary BF separator 11 is carried out in parallel with respect to a maximum of four cuvettes 100 (specimen in cuvette 100) by the four BF ports 51a to 51d.

The BF separating process is mainly configured by the pre-magnetism collecting (capturing of magnetic particles by magnetic force) process in the pre-magnetism collecting part 40, and the BF cleaning process (aspirating/discharging process of three times and aspirating process). Since the transfer of the cuvette 100 to the reaction unit 9, the pre-magnetism collecting part 40 and each BF port 51a to 51d is carried out by one transfer arm 30, the processing operation in each BF port 51a to 51d is carried out in parallel while shifting time. In the following, an example in which the cuvette 100 is transferred to the respective BF port in the order of the BF port 51a (port A), 51b (port B), 51c (port C), and 51d (port D), and the BF separating process is performed in such order will be described.

As shown in FIG. 10, the cuvette 100 is transferred from the reaction unit 9 to the pre-magnetism collecting part 40 at timing t1. The cuvette 100 arranged at the take-out position 230 (see FIG. 2) of the reaction unit 9 is taken out by the transfer arm 30 and transferred to the pre-magnetism collecting part 40. The transfer timing of the cuvette 100 to the pre-magnetism collecting part 40 is set for every predetermined time interval, where the transfer timing t32 of the next (second test) cuvette 100 is reached after the first (first test) cuvette 100 is transferred from the pre-magnetism collecting part 40 to the BF port 51a. When the cuvette 100 of the first test is transferred to the pre-magnetism collecting part 40, the pre-magnetism collecting process held in the pre-magnetism collecting part 40 is carried out during a predetermined time until timing t2. The magnetic particles are thereby captured at the bottom of the cuvette 100 set in the pre-magnetism collecting part 40 (see FIG. 9).

At timing t2, the transfer arm 30 (arm rotation motor 34 and arm raising and lowering motor 35) is driven, and the cuvette 100 of the first test is taken out from the pre-magnetism collecting part 40 and transferred to the empty BF port 51a (port A). The transfer timing to the BF port is set for every predetermined time interval. When the pre-magnetism collecting process of the next (second test) cuvette 100 is terminated after the first (first test) cuvette 100 is transferred from the pre-magnetism collecting part 40 to the BF port 51a, a timing t38 of transferring the next (second test) cuvette 100 to the BF port 51b (port B) is reached.

At timing t3, the BF cleaning process (aspirating/discharging process) is started on the cuvette of the first test. The BF cleaning process is configured by the aspirating/discharging processes (1) to (3) of three times performed at timing t3, t4, t5 set for every predetermined time interval, and the aspirating process performed at timing t6 after the termination of the aspirating/discharging process of three times with respect to one cuvette 100 (specimen). The BF cleaning process is the same in each BF port, and thus the BF cleaning process on the cuvette 100 of the first test in the BF port 51a (port A) will be described.

Figure 11:
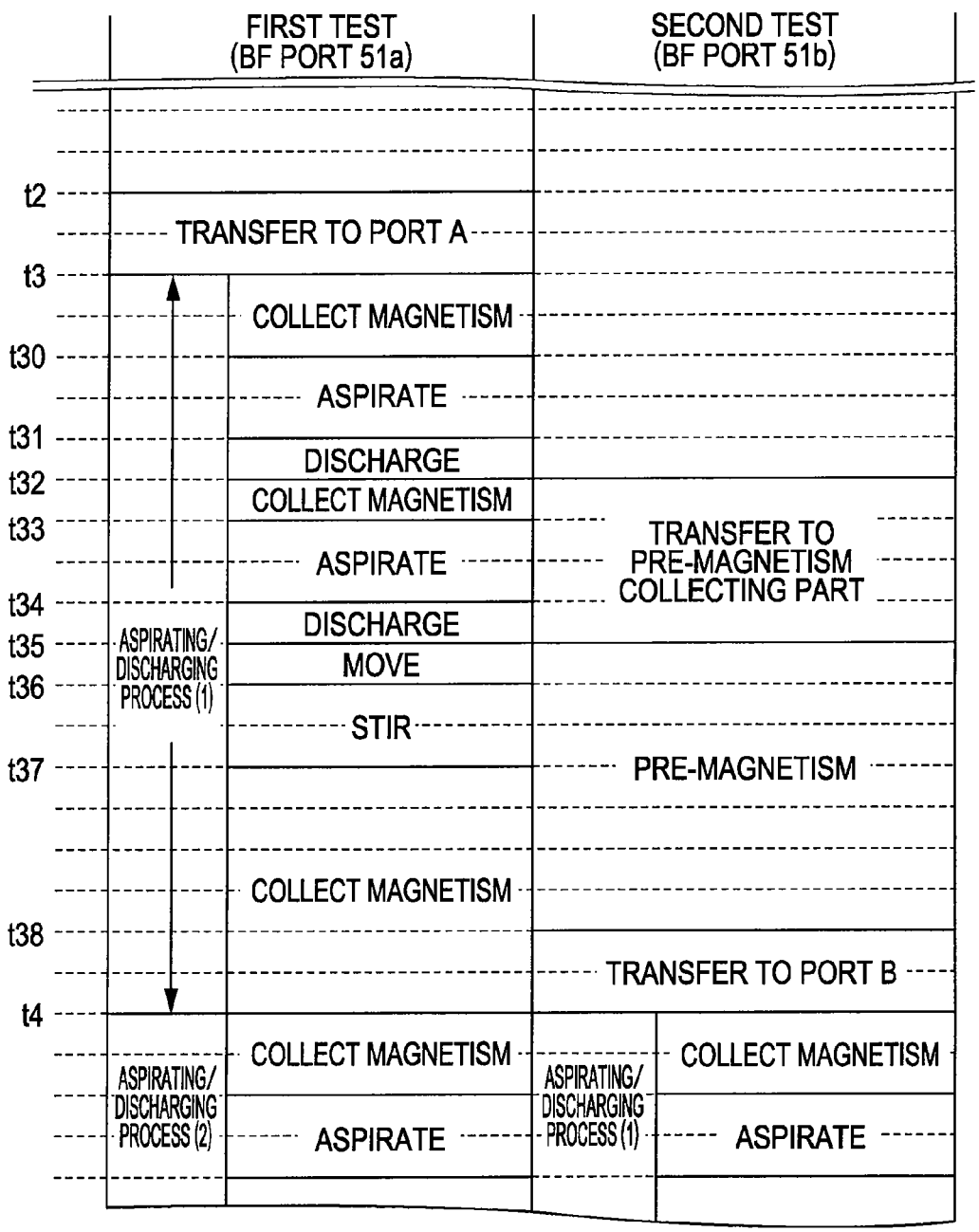
FIG. 11 is a timing chart for describing the BF cleaning process (aspirating/discharging process) in the BF separating process shown in FIG. 10.

As shown in FIG. 11, when the cuvette 100 of the first test is set in the BF port 51a at the start timing t3 of the BF cleaning process (aspirating/discharging process), the magnetism collecting process is performed until timing t30 in the BF port 51a. The magnetic particles are thereby captured on the inner side surface of the cuvette 100 (see FIG. 9) in the BF port 51a where the cuvette 100 is set. The movable installing part 50 moves so that the BF ports 51a to 51d are positioned at the aspirating/discharging positions (positions immediately below nozzles 61a to 61d) by the nozzles 61a to 61d during the magnetism collecting process.

At timing t30, the liquid inside the cuvette 100 of the first test is aspirated. Specifically, as shown in FIG. 9, the nozzle part 60 is lowered with the magnetic particles in the cuvette 100 captured, the nozzles 61a to 61d corresponding to each BF port 51a to 51d are advanced into the cuvette 100, and the liquid is aspirated by the nozzles 61a to 61d. Since the cuvette 100 is not set in the BF ports 51b to 51d in the first test (BF cleaning process is not started), the nozzles 61b to 61d are positioned up to the aspirating/discharging position in the BF ports 51b to 51d, respectively, but the aspirating operation is not carried out. This is the same in each process below, where the movement of the movable installing part 50, the raising and lowering movement of the nozzle part 60 and the stirring part 70 are carried out in synchronization in each BF port 51a to 51d, but the aspiration of the liquid, the discharging of the cleaning liquid, and the stirring are not carried out in the BF port in which the BF cleaning process has not started.

After the aspiration of the liquid, a predetermined amount of cleaning liquid is discharged from the nozzle 61a to the cuvette of the first test at timing t31, and then the nozzle part 60 is raised to retreat the nozzle 61a from inside the cuvette 100.

Thereafter, the magnetism collecting process is carried out at timing t32, and the liquid inside the cuvette 100 of the first test is aspirated at timing t33. At timing t34, a predetermined amount of cleaning liquid is discharged from the nozzle 61a, and then the nozzle part 60 is raised to retreat the nozzle 61a from inside the cuvette 100. That is, the magnetism collecting process, the aspiration of the liquid, and the discharging of the cleaning liquid are carried out two times respectively in one BF cleaning process. Timing t32 becomes the timing to transfer the cuvette of the second test to the pre-magnetism collecting part 40. Therefore, the movement process of the next (second test) cuvette 100 to the pre-magnetism collecting part 40 is started, and the pre-magnetism collecting is started from timing t35.

Thereafter, at timing t35, the stirring part 70 is lowered, each stirring catcher 71a to 71d is positioned at the cuvette take-out position, the movable installing part 50 is moved, and the cuvette 100 of the BF port 51a is gripped by the corresponding stirring catcher 71a.

At timing t36, the stirring part 70 (see FIG. 5) is raised, the gripped cuvette 100 is taken out from the BF port 51a, the stirring motor 74a (see FIG. 3) of the stirring catcher 71a is driven, and the stirring process is performed in a state the magnetic particles are not collected. Subsequently, the stirring part 70 is lowered, and the cuvette 100 is returned from the stirring catcher 71a to the corresponding BF port 51a.

After the stirring, the magnetism collecting process is carried out for a predetermined time (until next timing t4) to again capture the dispersed magnetic particles with the permanent magnets 54a and 54b at timing t37. One BF cleaning operation is then terminated.

While performing the magnetism collecting process, the transfer process of the next (second test) cuvette 100 to the BF port 51b (port B) is carried out at timing t38. Therefore, when reaching the timing t4 at when the aspirating/discharging process is started next, the aspirating/discharging process of the second time with respect to the cuvette 100 of the first test is carried out in the BF port 51a (port A), and the BF cleaning process (aspirating/discharging process of first time) with respect to the cuvette 100 of the second test is started in the BF port 51b (port B). Thus, during the BF cleaning process, the cuvette 100 is transferred to the next empty BF port (BF port 51b herein) not holding the cuvette 100 when the nozzle 61a (61b to 61d) is extracted from inside the cuvette 100. The content of the BF cleaning process is the same, and hence the same BF cleaning processing operation is executed in the BF port 51a and the BF port 51b in synchronization. The third subsequent tests are also the same, as shown in FIG. 10.

In the BF port 51a in which the aspirating/discharging operation is carried out three times, the aspirating process is carried out at the next timing t6. The aspirating process is carried out in synchronization with the BF cleaning process in other BF ports.

As shown in FIG. 12, in the aspirating process, the magnetism collecting process is performed in the BF port 51a at timing t6, and the liquid inside the cuvette 100 is aspirated by the nozzle 61a at timing t61.

At timing t62, the magnetism collecting process is again performed until timing t64 (discharging of cleaning liquid is not carried out) with respect to the cuvette of the first test, as opposed to the aspirating/discharging process. Timing t63 becomes the timing to transfer the cuvette 100 of the fifth test to the pre-magnetism collecting part 40. The cuvette 100 of the fifth test is thereby transferred from the reaction unit 9 to the pre-magnetism collecting part 40 by the transfer arm 30. The cuvette 100 of the fifth test becomes the next cuvette 100 to be set in the BF port 51a after the BF cleaning process on the cuvette 100 of the first test is completed.

At timing t64, the liquid inside the cuvette 100 of the first test is again aspirated. Thereafter, at timing t65, the magnetism collecting process is performed (discharging of liquid is not carried out) with respect to the cuvette of the first test, as opposed to the aspirating/discharging process.

At timing t66, the stirring part 70 is lowered, and the movable installing part 50 is moved to cause the corresponding stirring catcher 71a to grip the cuvette 100 of the BF port 51a.

Next, at timing t67, the stirring part 70 is raised, the gripped cuvette 100 is taken out from the BF port 51a and the stirring motor 74a of the stirring catcher 71a is driven so that the stirring process is performed. Subsequently, the stirring part 70 is lowered, and the cuvette 100 is returned from the each stirring catcher 71a to the corresponding BF port 51a.

The aspirating process is then terminated. As shown in FIG. 10, the transfer arm 30 (arm rotation motor 34 and arm raising and lowering motor 35) is driven at the transfer timing t7 to the reaction unit after the stirring, so that the cuvette 100 is taken out from the BF port 51a (port A) and the cuvette 100 is returned to the reaction unit 9 at a predetermined return position 240 (see FIG. 2). The BF cleaning process on the cuvette 100 of the first test is thereby completed.

When the cuvette 100 of the first test is returned to the reaction unit 9, the cuvette 100 of the fifth test is taken out from the pre-magnetism collecting part 40 by the transfer arm 30 and transferred to the empty BF port 51a (port A) at timing t71. In the BF port 51a (port A), the BF cleaning process on the next (fifth test) cuvette 100 (specimen) is started.

The BF cleaning process in each BF port 51a to 51d is started individually in the order set by the transfer arm 30, where some processes (aspirating/discharging process and aspirating process) are performed in parallel. The cuvette 100 is returned to the reaction unit 9 by the transfer arm 30 in the order the BF cleaning process is completed in each BF port 51a to 51d.

A control process in the BF separating process of the primary BF separator 11 of the immune analyzer 1 (measurement mechanism section 2) according to one embodiment of the present invention will now be described with reference to FIG. 2, FIG. 3, FIG. 5, and FIG. 10 to FIG. 16.

The control process in the BF separating process is configured by four processes performed at each timing shown in FIG. 10 to FIG. 12, where such processes are performed in parallel. Specifically, the four processes are a transfer process (take-out) of the cuvette 100 from the reaction unit 9 to the pre-magnetism collecting part 40, a transfer process of the cuvette 100 from the pre-magnetism collecting part 40 to the BF port (one of 51a to 51d), a BF cleaning process (aspirating/discharging process and aspirating process) in each BF port 51a to 51d, and a transfer process (return) of the cuvette 100 from the BF port (one of 51a to 51d) to the reaction unit 9. The BF separating processing operation by the primary BF separator 11 is performed when each portion of the primary BF separator 11 is controlled by the CPU 2a of the measurement mechanism section 2. The BF separating process by the secondary BF separator 12 is similar, and hence the description thereof will be omitted.

Figure 13:
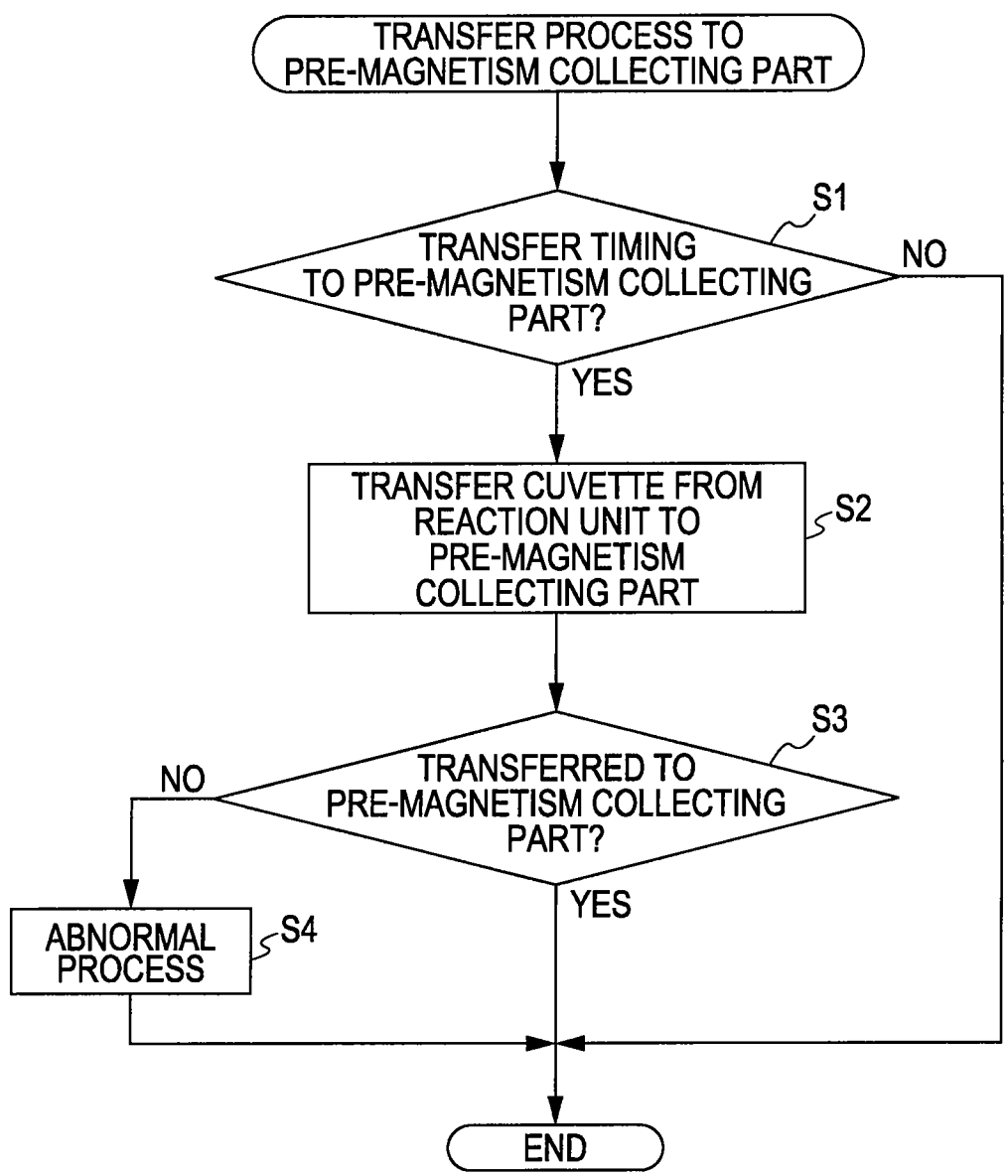
FIG. 13 is a flowchart showing a control operation of the transfer process to the pre-magnetism collecting part in the primary BF separator of the immune analyzer according to one embodiment of the present invention.

First, the transfer process of the cuvette 100 from the reaction unit 9 to the pre-magnetism collecting part 40 shown in FIG. 13 will be described.

In the transfer process to the pre-magnetism collecting part 40, whether or not the transfer timing (timing t1, timing t32, etc.) (see FIG. 10) of the cuvette 100 to the pre-magnetism collecting part 40 is determined by the CPU 2a in step S1. If not the transfer timing to the pre-magnetism collecting part 40, the transfer of the cuvette 100 from the reaction unit 9 to the pre-magnetism collecting part 40 is not performed.

If the transfer timing of the cuvette 100 to the pre-magnetism collecting part 40, in step S2, a predetermined cuvette 100 is taken out from the take-out position 230 (see FIG. 2) of the reaction unit 9 by the transfer arm 30 and set in the cuvette installing portion 41 of the pre-magnetism collecting part 40. In step S3, whether or not the cuvette 100 is set in the cuvette installing portion 41 of the pre-magnetism collecting part 40 is determined based on the detection result of the cuvette installing portion 41 by the cuvette sensor 43b.

If set in the cuvette installing portion 41, the transfer process of the cuvette 100 to the pre-magnetism collecting part 40 is terminated. If the detection by the cuvette sensor 43b cannot be recognized, the process proceeds to step S4, a predetermined abnormality (error) process is carried out, and the process is terminated. When the transfer process to the pre-magnetism collecting part 40 is performed every time the transfer timing to the pre-magnetism collecting part 40 is reached, the cuvette 100 to be processed is sequentially transferred from the take-out position 230 of the reaction unit 9 to the pre-magnetism collecting part 40.

Figure 14:
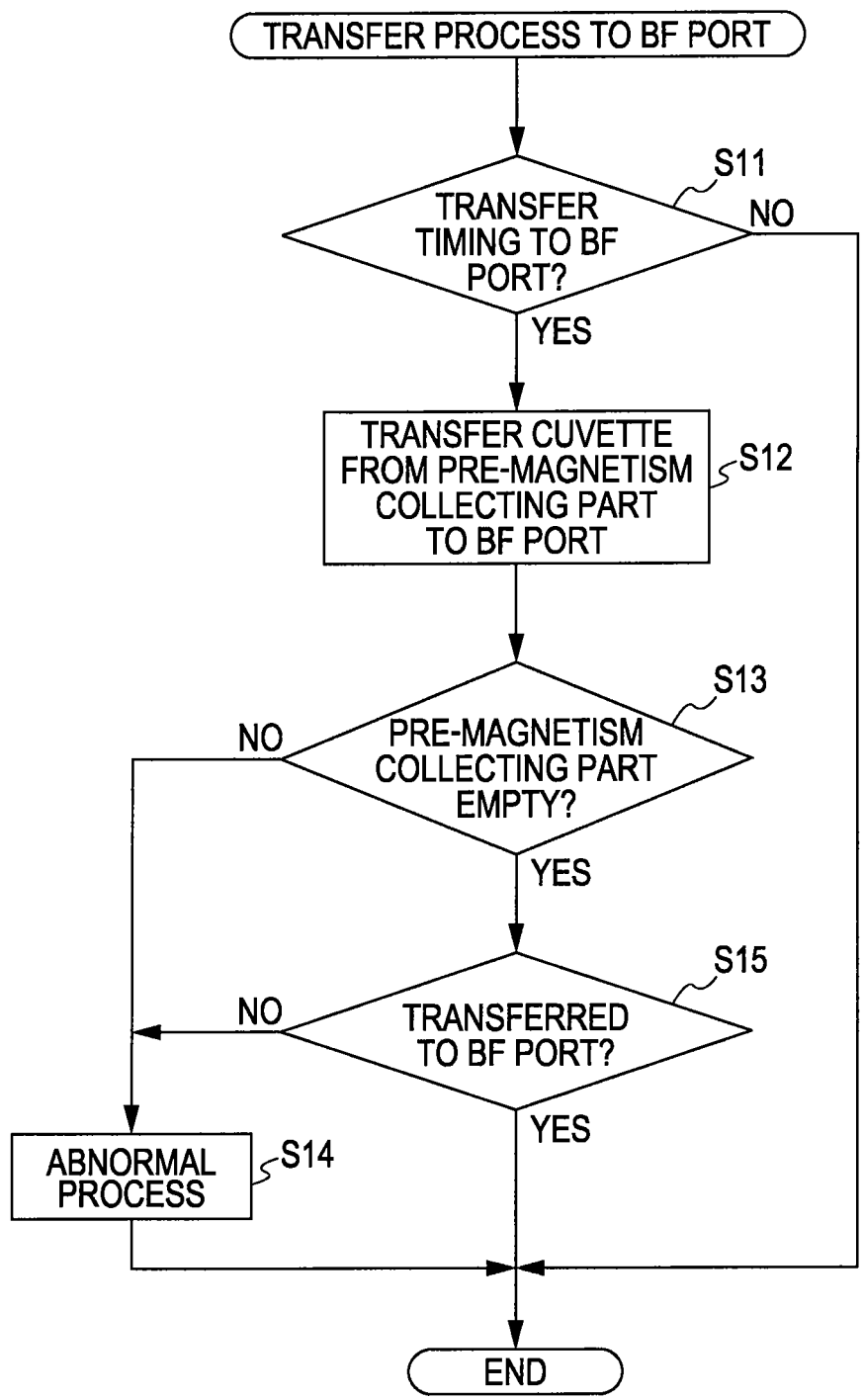
FIG. 14 is a flowchart showing a control operation of the transfer process to the BF port in the primary BF separator of the immune analyzer according to one embodiment of the present invention.

The transfer process of the cuvette 100 to the BF port shown in FIG. 14 will now be described.

First, in step S11, whether or not the transfer timing (timing t2, timing t38, etc.) (see FIG. 10) to the BF port (one of 51a to 51d) is determined. If not the transfer timing to the BF port, the transfer of the cuvette 100 from the pre-magnetism collecting part 40 to one of the BF ports 51a to 51d is not performed.

If the transfer timing to the BF port, the process proceeds to step S12, the transfer arm 30 (arm rotation motor 34 and arm raising and lowering motor 35) is driven, and the cuvette 100 is taken out from the cuvette installing portion 41 of the pre-magnetism collecting part 40 by the catcher 31 and transferred to the empty BF port in the order of BF port 51a, 51b, 51c, and 51d. In this case, as shown in FIG. 5, the horizontal movement motor 53 is controlled so that the BF port (one of 51a to 51d), or the transfer destination, is positioned on the arcuate trajectory C of the catcher 31, and the movable installing part 50 moves in synchronization with the transfer arm 30.

In step S13, whether or not the pre-magnetism collecting part 40 (cuvette installing portion 41) is empty (whether or not cuvette 100 is normally taken out) is determined based on the detection result of the cuvette installing portion 41 by the cuvette sensor 43b. If determined that the pre-magnetism collecting part 40 (cuvette installing portion 41) is not empty, the process proceeds to step S14, a predetermined abnormality (error) process is carried out, and then the process is terminated.

If determined that the pre-magnetism collecting part 40 (cuvette installing portion 41) is empty, the process proceeds to step S15, and whether or not the cuvette 100 is transferred to the BF port (one of 51a to 51d) of the transfer destination based on the detection result of the BF port (one of 51a to 51d) of the transfer destination by the cuvette sensor 55b (see FIG. 3). If determined as transferred to the BF port (one of 51a to 51d) of the transfer destination, the transfer process of the cuvette 100 to the relevant BF port (one of 51a to 51d) is terminated. If the detection of the BF port (one of 51a to 51d) or the transfer destination by the cuvette sensor 55b is not recognized, the process proceeds to step S14, a predetermined abnormality (error) process is carried out, and then the process is terminated. When the transfer process to the BF port is performed every time the transfer timing to the BF port is reached, the cuvette 100 to be processed is transferred in order from the pre-magnetism collecting part 40 to the empty BF port (one of 51a to 51d).

Figure 15:
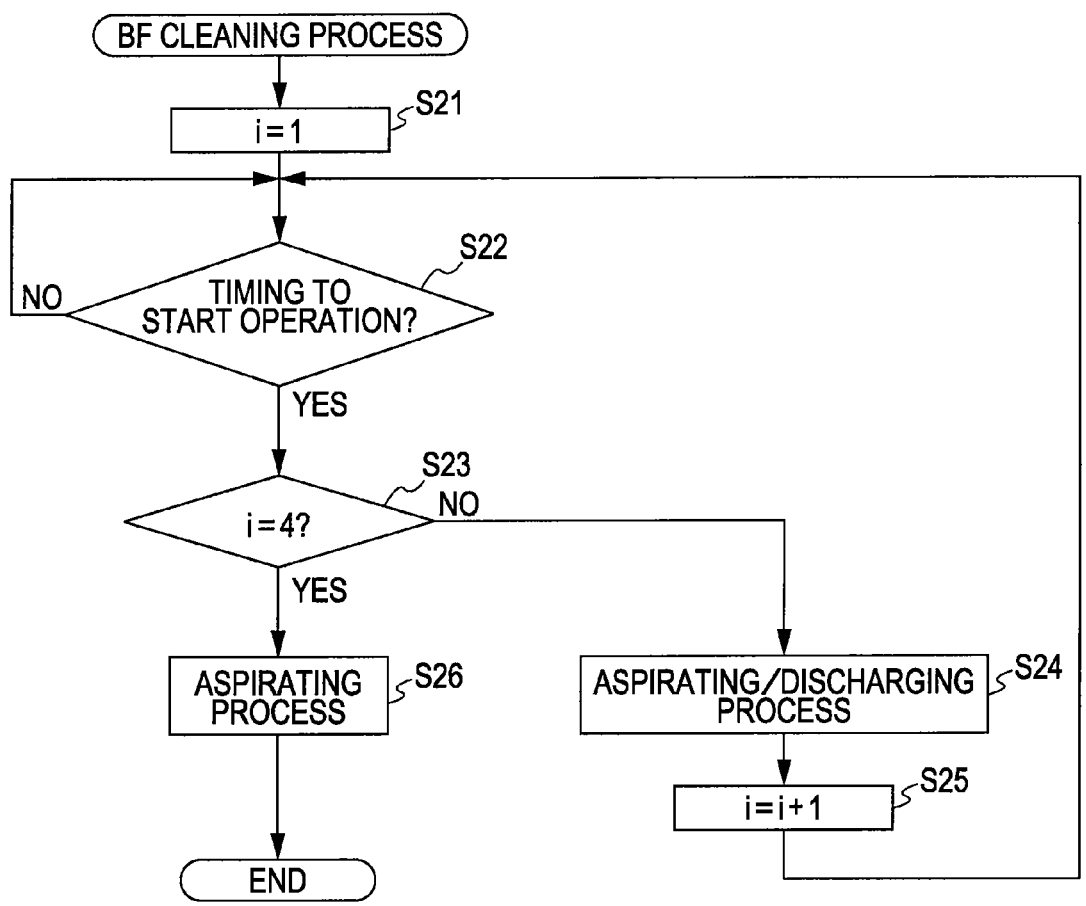
FIG. 15 is a flowchart showing a control operation of the BF cleaning process performed in each BF port of the primary BF separator of the immune analyzer according to one embodiment of the present invention.

The BF cleaning process in the BF ports 51a to 51d shown in FIG. 15 will now be described. As described above, the BF cleaning process is configured by the aspirating/discharging processes (1) to (3) of three times, and the aspirating process (see FIG. 11) after the termination of the aspirating/discharging process.

In the BF cleaning process, a variable i indicating the number of executions of the aspirating/discharging process is set to "1" (initialization) in step S21. In step S22, whether or not the start timing (timing t3, t4, t5, t6, etc.) of the processing operation is determined. If not the start timing of the processing operation, the determination of step S22 is repeated until the next operation start timing.

When the start timing of the processing operation is reached, the process proceeds to step S23 and whether or not the variable i is "4" is determined. If the variable i is not "4", the process proceeds to step S24, and the aspirating/discharging process is performed. As shown in FIG. 11, in the aspirating/discharging process, each part of the movable installing part 50, the nozzle part 60, the stirring part 70, and the like is controlled such that each process is performed at a predetermined timing.

When the aspirating/discharging process is terminated, "1" is added to the variable i indicating the number of executions of the aspirating/discharging process in step S25. The process then proceeds to step S22, and the next operation start timing is waited. Since the variable i becomes "4" when steps S22 to S25 are repeated three times (aspirating/discharging process is performed three times), the process proceeds from step S23 to step S26.

In step S26, the aspirating process is carried out. As shown in FIG. 12, in the aspirating process, each part of the movable installing part 50, the nozzle part 60, the stirring part 70, and the like is controlled such that each process is performed at a predetermined timing. The BF cleaning process in the BF ports 51a to 51d is completed when the aspirating process of step S26 is completed. The BF cleaning process in the BF ports 51a to 51d is determined for each BF port 51a to 51d, so that the stage of the process in each BF port 51a to 51d (which number of aspirating/discharging process) differs depending on the BF port as shown in FIG. 10.

Figure 16:
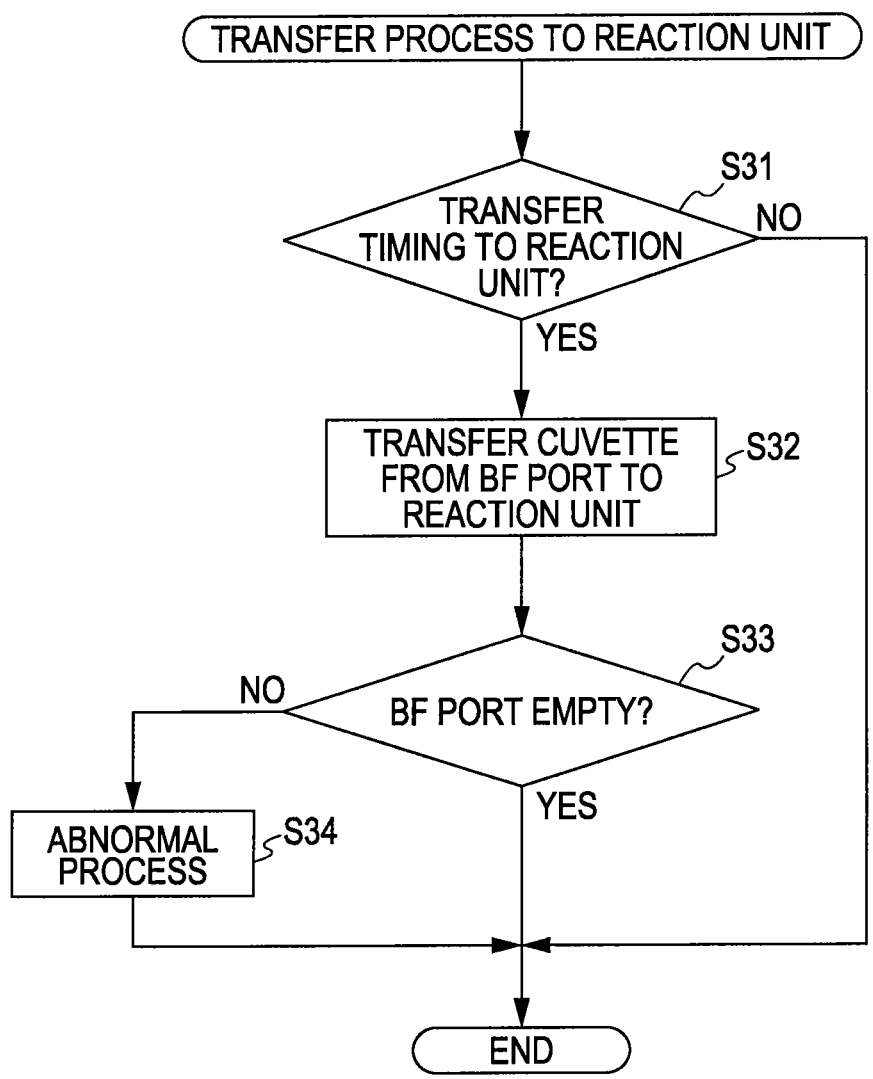
FIG. 16 is a flowchart showing a control operation of the transfer process to the reaction unit in the primary BF separator of the immune analyzer according to one embodiment of the present invention.

The transfer process of the cuvette 100 from the BF port 51a to 51d to the reaction unit 9 shown in FIG. 16 will now be described.

In the transfer process to the reaction unit 9, whether or not the transfer timing (timing t7, etc.) (see FIG. 10) of the cuvette 100 to the reaction unit 9 is determined in step S31. If not the transfer timing to the reaction unit 9, the transfer of the cuvette 100 from the BF port 51a to 51d to the reaction unit 9 is not performed.

If the transfer timing of the cuvette 100 to the reaction unit 9, in step S32, the movable installing part 50 is driven and the BF port 51a to 51d in which the cuvette 100 to be transferred is set is positioned on the arcuate trajectory C (see FIG. 5) of the catcher 31, and the transfer arm 30 (arm rotation motor 34 and arm raising and lowering motor 35) is also driven and the cuvette 100 to be transferred of the BF port 51a to 51d is taken out by the catcher 31. The cuvette 100 is set in the cuvette holder 9a of the reaction unit 9 at a predetermined return position 240 (see FIG. 2) on the arcuate trajectory C.

In step S33, whether or not the BF port 51a to 51d is empty (whether or not the cuvette is normally taken out) is determined based on the detection result of the BF port 51a to 51d holding the cuvette 100 to be transferred by the cuvette sensor 55b.

If the BF port 51a to 51d is empty, the transfer process of the cuvette 100 from the BF port 51a to 51d to the reaction unit 9 is terminated. If the detection of the BF port 51a to 51d holding the cuvette 100 to be transferred by the cuvette sensor 55b (detection of cuvette 100 is not present) is not recognized, determination is made that the BF port 51a to 51d is not empty, whereby the process proceeds to step S34, a predetermined abnormality (error) process is carried out, and then the process is terminated. When the transfer process to the reaction unit 9 is performed every time the transfer timing to the reaction unit 9 is reached, the cuvette is transferred from the BF port 51a to 51d to the reaction unit 9 in order from the cuvette 100 in which the BF cleaning process is completed.

Therefore, in the present embodiment, a plurality of BF ports 51a to 51d, and a nozzle part 60 with a plurality of nozzles 61a to 61d arranged in correspondence with the plurality of BF ports 51a to 51d are arranged, and the BF separating process is carried out in parallel by the respective BF port 51a to 51d and the nozzle 61a to 61d corresponding to each BF port 51a to 51d, so that the BF separating process can be carried out in parallel with respect to a plurality of cuvettes 100 and the sample processing ability of the immune analyzer 1 can be enhanced. Furthermore, according to the configuration in which the BF separating process with respect to the respective cuvette 100 arranged in the respective BF port 51a to 51d is individually completed by the respective nozzle 61a to 61d corresponding to the respective BF port 51a to 51d, the BF separating process on one cuvette 100 can be completed by the nozzle 61a to 61d corresponding to the BF port 51a to 51d in which the cuvette 100 is arranged, so that a situation where only a specific nozzle of the plurality of nozzles 61a to 61d is contaminated at high degree than the other nozzles can be avoided. Thus, even if the BF separating process with respect to a plurality of cuvettes 100 is carried out in parallel using a plurality of nozzles 61a to 61d, a long time is not required on only the cleaning of a specific nozzle 61a to 61d, and the occurrence of carry-over to the next sample can be suppressed. Thus, in the immune analyzer 1 according to the present embodiment, the sample processing ability of the immune analyzer 1 can be enhanced while suppressing the occurrence of carry-over.

In the present embodiment, as described above, the CPU 2a controls the nozzle part 60 such that BF separating process is completed by carrying out the discharging of the cleaning liquid to the respective cuvette 100 arranged in the respective BF port 51a to 51d and the aspiration of liquid over plural times with each corresponding nozzle 61a to 61d. According to such configuration, in the respective BF port 51a to 51d, the discharging of the cleaning liquid to the cuvette 100 and the aspiration of the liquid in the cuvette 100 are repeated over plural times with the corresponding nozzle 61a to 61d, and hence the contamination attached to the nozzles 61a to 61d can be reduced in the course of lowering the concentration of the unreacted substance in the cuvette 100. As a result, in the respective BF port 51a to 51d, the contamination attached to the nozzles 61a to 61d at the time point the BF separating process is completed is reduced, so that the time required for the cleaning of the nozzles 61a to 61d can be reduced.

In the present embodiment, as described above, one nozzle raising and lowering motor 63 commonly used for the up and down movement of the plurality of nozzles 61a to 61d is arranged. According to such configuration, the device configuration can be simplified since the plurality of nozzles 61a to 61d can be moved up and down with a common drive unit (nozzle raising and lowering motor 63).

In the present embodiment, as described above, the CPU 2a controls the transfer arm 30 such that other cuvettes 100 are transferred to the BF ports 51a to 51d in which the cuvette 100 is not arranged when the nozzles 61a to 61d corresponding to the BF ports 51a to 51d are moved upward and the cuvette 100 is taken out in the middle of the BF separating process with respect to the cuvette 100 arranged in the BF ports 51a to 51d. According to such configuration, when the plurality of nozzles 61a to 61d that move up and down in synchronization are moved upward and the nozzle 100 is taken out, the cuvette 100 is to be transferred to the BF port (one of 51a to 51d) in which the cuvette 100 is not arranged, and thus the plurality of cuvettes 100 can be sequentially transferred to the BF ports 51a to 51d in the middle of the BF separating process while simplifying the control of the nozzle raising and lowering motor 63.

In the present embodiment, as described above, one stirring part raising and lowering motor 73 commonly used for the up and down movement of the plurality of stirring catchers 71a to 71d is arranged. According to such configuration, the device configuration can be simplified since the plurality of stirring catchers 71a to 71d can be moved up and down with a common drive unit (stirring part raising and lowering motor 73).

In the present embodiment, as described above, the CPU 2a controls the transfer arm 30 so that the cuvette 100 is transferred to one of the BF ports 51a to 51d of the primary BF separator 11 after the cuvette 100 is arranged in the pre-magnetism collecting part 40, and controls the nozzle part 60 to start the aspiration of the liquid in the cuvette 100 arranged in the BF port (one of 51a to 51d) of the transfer destination. According to such configuration, the magnetic particles in the cuvette 100 can be captured in advance with the pre-magnetism collecting part 40 before the cuvette 100 is transferred to each BF port 51a to 51d, and thus the time required to capture the magnetic particles in each BF port 51a to 51d can be reduced. As a result, the aspirating operation of the liquid in the cuvette 100 can be started earlier.

Furthermore, in the present embodiment, as described above, the cuvette 100 is transported to one of the BF ports 51a to 51d by the transfer arm 30 after the plurality of cuvettes 100 pass through the same transport path (transport path by reaction unit 9 and transfer arm 30). According to such configuration, the transport path of the cuvette 100 up to the transfer arm 30 for transferring the container to a plurality of BF ports 51a to 51d can be commonly used, so that the device configuration and the operation control of the immune analyzer 1 can be simplified in the configuration in which the BF separating process is carried out in parallel in each of the plurality of BF ports 51a to 51d.

In the present embodiment, as described above, the CPU 2a controls the horizontal movement motor 53 such that the BF ports 51a to 51d of the primary BF separator 11 are positioned on the trajectory of the rotational movement of the cuvette 100 held in the transfer arm 30. According to such configuration, the cuvette 100 can be transferred to each of the plurality of BF ports 51a to 51d by moving the BF ports 51a to 51d onto the arcuate trajectory C of the transfer arm 30 even with a simple configuration of rotating the transfer arm 30 about the rotation shaft 36.

In the present embodiment, as described above, the CPU 2a is configured to control the arm rotation motor 34 so as to take out the cuvette 100 at the take-out position 230 of the reaction unit 9 with the transfer arm 30, transfer the cuvette 100 taken out to the BF ports 51a to 51d of the primary BF separator 11 with the transfer arm 30, and take out the cuvette 100 from the BF ports 51a to 51d of the primary BF separator 11 with the transfer arm 30 and transfer the same to the return position 240 of the reaction unit 9. According to such configuration, the transfer of the cuvette 100 from the reaction unit 9 to one of the BF ports 51a to 51d and the transfer of the cuvette 100 from the BF ports 51a to 51d to the reaction unit 9 can be carried out with the common transfer arm 30, and thus the device configuration can be further simplified.

In the present embodiment, the CPU 2a controls the arm rotation motor 34 to sequentially take out a plurality of cuvettes 100 from the take-out position 230 with one transfer arm 30, sequentially transfer the cuvettes 100 that are taken out to each BF port 51a to 51d of the primary BF separator 11, and transfer the cuvettes in order from the cuvette 100 completed with the BF separating process to the return position 240 with one transfer arm 30, and executes the BF separating process partially in parallel with each BF port 51a to 51d and the nozzle 61a to 61d corresponding to each BF port 51a to 51d. According to such configuration, the cuvette 100 can be sequentially transferred to the respective BF port 51a to 51d and the cuvette 100 completed with the BF separating process can be sequentially returned to the reaction unit 9 with one transfer arm 30, whereby the device configuration can be simplified. In this case as well, the BF separating process can be started from the BF ports 51a to 51d in which the cuvette 100 is arranged and the process can be carried out partially in parallel in each BF port 51a to 51d so that the sample processing ability of the immune analyzer 1 can be enhanced.

The embodiments disclosed herein are illustrative and should not be construed as being restrictive in all aspects. The scope of the present invention is defined by the scope of the claims rather than by the description of the embodiment, and meaning equivalent to the claims and all modifications within the scope is encompassed herein.

For instance, an example in which the analyzer of the present invention is applied to the immune analyzer 1 has been described in the embodiment described above, but the present invention is not limited thereto. The present invention can be applied as long as it is an analyzer that analyzes using a reagent containing magnetic particles, and can be applied even to an analyzer other than the immune analyzer. For instance, the present invention may be applied to an apparatus for extracting a specific DNA using the BF separating process.

An example in which one pre-magnetism collecting part is arranged has been described in the embodiment described above, but the present invention is not limited thereto. In the present invention, a plurality of pre-magnetism collecting parts may be arranged.

An example in which the pre-magnetism collecting part is arranged in the primary BF separator (secondary BF separator) has been described in the above embodiment, but the present invention is not limited thereto. The present invention may adopt a configuration in which the pre-magnetism collecting part is arranged separate from the primary (secondary) BF separator, and the cuvette in which the magnetism collecting process is carried out in advance in the pre-magnetism collecting part is transferred to the primary (secondary) BF separator.

An example in which four BF ports are arranged has been described in the above embodiment, but the present invention is not limited thereto. In the present invention, two to three, or five or more BF ports may be arranged.

An example in which the cuvette is transferred to each BF port by one transfer arm arranged in the primary (secondary) BF separator has been described in the above embodiment, but the present invention is not limited thereto. In the present invention, a plurality of transfer arms may be arranged. The transfer arm may be arranged separate from the primary (secondary) BF separator. For instance, the transfer arm common to the primary BF separator and the secondary BF separator may be arranged separate from the primary (secondary) BF separator.

An example in which the cuvette set in the cuvette installing portion is taken out by the catcher of the transfer arm and transferred to each BF port has been described in the above embodiment, but the present invention is not limited thereto. For instance, the cuvette may be transferred from the cuvette installing portion to each BF port by a container transfer unit such as a conveyor.

An example in which four BF ports, four nozzles, and four stirring catchers are respectively moved by one horizontal movement motor, one nozzle raising and lowering motor, and one stirring part raising and lowering motor has been described in the above embodiment, but the present invention is not limited thereto. In the present invention, a drive unit may be individually arranged in each BF port, nozzle, and stirring catcher so that they can move independent from each other. For instance, only the BF port may be individually moved.

An example in which the operation control of each unit related to the BF separating process is carried out by the CPU 2a of the measurement mechanism section 2 has been described in the above embodiment, but the present invention is not limited thereto. For instance, the CPU 4a of the control device 4 may carry out the operation control of each unit related to the BF separating process, or both the CPU 4a of the control device 4 and the CPU 2a of the measurement mechanism section 2 may carry out the operation control in cooperation.

An example in which the BF cleaning process in each BF port is completed by having the corresponding nozzle carry out the discharging of the cleaning liquid and the aspiration of the liquid over a plurality of times has been described in the above embodiment, but the present invention is not limited thereto. In the present invention, the corresponding nozzle may carry out the discharging of the cleaning liquid and the aspiration of the liquid only once.

Similarly, an example in which the BF cleaning process in each BF port is configured by the aspirating/discharging process of three times and the aspirating process of one time has been described in the above embodiment, but the present invention is not limited thereto. For instance, the aspirating/discharging process may be once or twice, or may be four or more times. The aspirating process may be carried out over a plurality of times, or the aspirating process may not be carried out. The content of the BF cleaning process may be set according to the performance of the device (primary (secondary) BF separator).

An example in which the transport path of the cuvette up to the pre-magnetism collecting part of before the cuvette is transported to one of the four BF ports is configured to be the same has been described in the above embodiment, but the present invention is not limited thereto. In the present invention, the pre-magnetism collecting part may be arranged in plurals, and only the transport path to the reaction unit may be made the same. Furthermore, the transport path may not be made common, and the cuvette may be transported to each BF port in different transport paths.

What is claimed is:

1. A sample analyzing method of analyzing a liquid specimen containing biological complexes formed from target substances bonded with magnetic particles, the method being carried out with a target substance separating process for magnetically separating the biological complexes from substances other than the biological complexes in the liquid specimen, the target substance separating process comprising steps of:
- (a) receiving at a preliminary BF separator a container having an amount of the liquid specimen therein and performing at the preliminary BF separator magnetic separation on the received container, using a magnet arranged to the preliminary BF separator, to magnetically collect the magnetic particles at a location in the received container;
- (b) after the magnetic separation is performed at the preliminary BF separator, transferring the container by a container transfer unit from the preliminary BF separator to an available one of a plurality of ports;
- (c) executing the magnetic separation on the containers separately in parallel at at least some of the plurality of ports, using a group of magnets arranged, respectively, to the plurality of ports and each used to perform the magnetic separation on the container received at the corresponding port in order to magnetically collect the magnetic particles at a location in the container;
- (d) aspirating liquid from the containers separately in parallel at at least some of the plurality of ports, using a group of nozzles arranged, respectively, to the plurality of ports and each configured to discharge a cleaning liquid into and aspire liquid from the container received at the corresponding port;
- (e) discharging the cleaning liquid in the containers separately in parallel at at least some of the plurality of ports; and
- (f) repeating above steps (c), (d) and (e) at multiple cycles on each of the containers while it stays at its port.

2. The sample analyzing method of claim 1, wherein steps (d) and (e) are performed separately in parallel on the containers at at least some of the plurality of ports.

3. The sample analyzing method of claim 2, wherein above steps (d) and (e) are performed at multiple cycles separately in parallel on the containers at at least some of the plurality of ports so that at one moment, a (N−1)th cycle of steps (d) and (e) is performed at one port while a Nth cycle of steps (d) and (e) is performed at another port.

4. The sample analyzing method of claim 1, further comprising: (g) transferring by the container transfer unit the container to the preliminary BF separator, wherein step (a) is executed after step (g) is executed.

5. The sample analyzing method of claim 4, wherein step (b) is executed while steps (c), (d) and (e) are being executed at at least some of the plurality of ports other than the available one of the ports.

6. The sample analyzing method of claim 1, further comprising moving the group of nozzles by a common drive unit up from the containers at at least some of the plurality of ports and down thereinto.

7. The sample analyzing method of claim 6, wherein
moving the group of nozzles comprises moving the group of nozzles together in synchronization; and
step (b) comprises transferring the container from the preliminary BF separator to the available one of the ports when the group of nozzles are moved up during the target substance separating process being performed at at least some of the plurality of ports other than the available one of the ports.

8. The sample analyzing method of claim 1, further comprising:
gripping the containers separately by a group of grip units arranged, respectively, to the plurality of ports; and
moving the group of grip units by a second common drive unit to stir the cleaning liquid and the magnetic particles bonding with the target substance in the containers received at at least some of the plurality of ports.

9. The sample analyzing method of claim 1, wherein
step (a) is executed while executing the target substance separating process on another container at one of the plurality of ports.

10. The sample analyzing method of claim 1, wherein
the container transfer unit includes: an arm configured to hold the container; and a rotation drive unit configured to rotate the arm in a horizontal plane around a predetermined rotation shaft, and
the method further comprises moving the plurality of ports in the horizontal plane by a horizontal drive unit to position a respective plurality of ports in alignment with a circular path of the container rotated by the arm of the container transfer unit.

11. The sample analyzing method of claim 10, further comprising:
conveying the containers by a reaction unit along a path;
adding a reagent containing the magnetic particles in the containers while conveying the container by the reaction unit along the path;
picking up the conveyed container by the arm of the container transfer unit from the reaction unit at a first predetermined position in the path;
transferring the picked up container to the preliminary BF separator; and
picking up the container by the arm from one of the plurality of ports and returning the container to the reaction unit at a second predetermined position in the path.

12. The sample analyzing method of claim 11, wherein the arm is the only arm provided to the container transfer unit, and the method further comprises:
operating the arm to pick up the containers one at a time from the reaction unit at the first predetermined position and sequentially transfer the picked up containers to the preliminary BF separator; and
further operating the arm to pick up the containers one at a time from the plurality of ports and sequentially return the picked up containers to the reaction unit at the second predetermined position in an order in which the containers complete the target substance separating process performed thereon.

13. The sample analyzing method of claim 1, further comprising optically detecting, by an optical detector, the target substance contained in the complex separated by the target substance separating process.

* * * * *